US011179132B2

(12) United States Patent
Yu et al.

(10) Patent No.: US 11,179,132 B2
(45) Date of Patent: Nov. 23, 2021

(54) HELICAL CONE-BEAM COMPUTED TOMOGRAPHY IMAGING WITH AN OFF-CENTERED DETECTOR

(71) Applicant: Accuray, Inc., Sunnyvale, CA (US)

(72) Inventors: Zhicong Yu, Highland Hts., OH (US); Daniel Gagnon, Twinsburg, OH (US)

(73) Assignee: Accuray, Inc., Sunnyvale, CA (US)

( * ) Notice: Subject to any disclaimer, the term of this patent is extended or adjusted under 35 U.S.C. 154(b) by 14 days.

(21) Appl. No.: 16/694,190

(22) Filed: Nov. 25, 2019

(65) Prior Publication Data
US 2020/0170585 A1 Jun. 4, 2020

Related U.S. Application Data

(60) Provisional application No. 62/773,712, filed on Nov. 30, 2018, provisional application No. 62/773,700, (Continued)

(51) Int. Cl.
*A61B 6/00* (2006.01)
*A61B 6/02* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01); *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01);
(Continued)

(58) Field of Classification Search
CPC ....... A61B 6/032; A61B 6/027; A61B 6/5205; A61B 6/4805; G06T 11/005
See application file for complete search history.

(56) References Cited

U.S. PATENT DOCUMENTS 4,190,773 A 2/1980 Braden et al.
5,615,279 A 3/1997 Yoshioka et al.
(Continued)

FOREIGN PATENT DOCUMENTS

DE 10 2006 007058 A1 7/2007
EP 1062914 A1 12/2000
(Continued)

OTHER PUBLICATIONS

International Search Report and Written Opinion from PCT/US2019/063080 dated Mar. 16, 2020.
(Continued)

*Primary Examiner* — Courtney D Thomas
(74) *Attorney, Agent, or Firm* — Calfee, Halter & Griswold LLP

(57) ABSTRACT

An x-ray imaging apparatus and associated methods are provided to process projection data from an offset detector during a helical scan, including view completion. The detector may be offset in the channel and/or axial direction. Projection data measured from a current view is combined with projection data measured from at least one conjugate view to reconstruct a target image. A two-dimensional aperture weighting scheme is used to address data redundancy.

20 Claims, 15 Drawing Sheets

Related U.S. Application Data filed on Nov. 30, 2018, provisional application No. 62/796,831, filed on Jan. 25, 2019, provisional application No. 62/800,287, filed on Feb. 1, 2019, provisional application No. 62/801,260, filed on Feb. 5, 2019, provisional application No. 62/813,335, filed on Mar. 4, 2019, provisional application No. 62/821,116, filed on Mar. 20, 2019, provisional application No. 62/836,357, filed on Apr. 19, 2019, provisional application No. 62/836,352, filed on Apr. 19, 2019, provisional application No. 62/843,796, filed on May 6, 2019, provisional application No. 62/878,364, filed on Jul. 25, 2019.

(51) Int. Cl.

| | | |
|---|---|---|
| *G06T 11/00* | (2006.01) | |
| *A61B 6/03* | (2006.01) | |
| *A61B 6/06* | (2006.01) | |
| *A61N 5/10* | (2006.01) | |
| *A61B 6/08* | (2006.01) | |
| *G06T 7/30* | (2017.01) | |
| *A61B 5/055* | (2006.01) | |
| *A61B 6/04* | (2006.01) | |

(52) U.S. Cl.
CPC .............. *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | | |
|---|---|---|---|
| 6,233,478 | B1 | 5/2001 | Liu |
| 6,307,909 | B1 | 10/2001 | Flohr et al. |
| 7,050,528 | B2 | 5/2006 | Chen |
| 7,108,421 | B2 | 9/2006 | Gregerson et al. |
| 7,660,380 | B2 | 2/2010 | Boese et al. |
| 8,116,430 | B1 | 2/2012 | Shapiro et al. |
| 8,467,497 | B2 | 6/2013 | Lu et al. |
| 8,588,363 | B2 | 11/2013 | Flohr |
| 9,400,332 | B2 | 7/2016 | Star-Lack et al. |
| 2003/0076927 | A1 | 4/2003 | Shigeyuki et al. |
| 2004/0091079 | A1 | 5/2004 | Zapalac |
| 2004/0202360 | A1 | 10/2004 | Besson |
| 2005/0053188 | A1 | 3/2005 | Gohno |
| 2005/0251029 | A1 | 11/2005 | Khamene et al. |
| 2006/0109954 | A1 | 5/2006 | Gohno |
| 2006/0262894 | A1 | 11/2006 | Bernhadt et al. |
| 2007/0127621 | A1 | 6/2007 | Grass et al. |
| 2007/0189444 | A1 | 8/2007 | Van Steven-Daal et al. |
| 2008/0112532 | A1 | 5/2008 | Schlomka et al. |
| 2009/0080603 | A1 | 3/2009 | Shukla et al. |
| 2009/0135994 | A1 | 5/2009 | Yu et al. |
| 2009/0161826 | A1 | 6/2009 | Gertner et al. |
| 2009/0225932 | A1 | 9/2009 | Zhu et al. |
| 2009/0283682 | A1 | 11/2009 | Star-Lack et al. |
| 2010/0046819 | A1 | 2/2010 | Noo et al. |
| 2010/0208964 | A1 | 8/2010 | Wiegert et al. |
| 2011/0142312 | A1 | 6/2011 | Toth et al. |
| 2012/0014582 | A1* | 1/2012 | Schaefer ................ A61B 6/032 382/131 |
| 2012/0207370 | A1 | 8/2012 | Fahimian et al. |
| 2012/0263360 | A1 | 10/2012 | Zhu et al. |
| 2012/0294504 | A1 | 11/2012 | Kyriakou |
| 2013/0101082 | A1 | 4/2013 | Jordan et al. |
| 2013/0294570 | A1* | 11/2013 | Hansis ................ G06K 9/6202 378/4 |
| 2014/0018671 | A1 | 1/2014 | Li et al. |
| 2014/0086383 | A1 | 3/2014 | Huwer et al. |
| 2015/0297165 | A1 | 10/2015 | Tanaka et al. |
| 2015/0305696 | A1 | 10/2015 | Yamakawa et al. |
| 2016/0016009 | A1 | 1/2016 | Manzke et al. |
| 2016/0120486 | A1 | 5/2016 | Goto |
| 2016/0262709 | A1 | 9/2016 | Siewerdsen et al. |
| 2017/0000428 | A1 | 1/2017 | Goto |
| 2017/0197098 | A1 | 7/2017 | Hirasawa et al. |
| 2017/0205360 | A1 | 7/2017 | Cinquin et al. |
| 2017/0332982 | A1 | 11/2017 | Koehler et al. |
| 2018/0070894 | A1 | 3/2018 | Osaki et al. |
| 2018/0192978 | A1 | 7/2018 | Naylor |
| 2018/0345042 | A1 | 12/2018 | Voronenko et al. |
| 2020/0121267 | A1 | 4/2020 | Deutschmann |
| 2021/0165122 | A1 | 6/2021 | Morton |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.
International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.

(56) References Cited

OTHER PUBLICATIONS

Spearman, et al. Effect of Automated Attenuation-Based Tube Voltage Selection on Radiation Dose at CT: An Observational Study on a Global Scale11 , Radiology, vol. 279, No. Apr. 1, 2016 (Apr. 1, 2016) , pp. 167-174, XP055734550.

Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.

Wang et al., "A General Cone-Beam Reconstruction Algorithm," IEEE Transactions on Medical Imaging, vol. 12, No. 3 Sep. 1, 1993.

Wang, "X-Ray Micro-CT With a Displaced Detector Array," Medical Physics, vol. 29, No. 7, Jul. 1, 2002.

Office Action from U.S. Appl. No. 16/694,145 dated Mar. 17, 2021, 10 pages.

Office Action from U.S. Appl. No. 16/694,192 dated Jun. 10, 2021, 10 pages.

Office Action from U.S. Appl. No. 16/694,202 dated Apr. 9, 2021, 12 pages.

Restriction Requirement from U.S. Appl. No. 16/694,210 dated Jun. 10, 2021, 6 pages.

Office Action from U.S. Appl. No. 16/694,218 dated Apr. 15, 2021, 7 pages.

Office Action from U.S. Appl. No. 16/694,230 dated Apr. 1, 2021, 6 pages.

Clackdoyle, et al.. Data consistency conditions for truncated fanbeam and parallel projections, Med. Phys. Feb. 2015, pp. 831-845, vol. 42, No. 2.

Defrise, et al., A solution to the long-object problem in helical cone-beam tomography, Physics in Medicine and Biology, 2000, pp. 623-643, vol. 45.

Hsieh, et al., A novel reconstruction algorithm to extend the CT scan field-of-view, Med. Phys., Sep. 2004, pp. 2385-2391, vol. 31, No. 9.

Katsevich, A., An improved exact filtered backprojection algorithm for spiral computed tomography, Advances in Applied Mathematics, 2004, pp. 691-697, vol. 32.

Kudo et al., Exact and approximate algorithms for helical cone-beam CT, Physics in Medicine and Biology, 2004, pp. 1-26, vol. 49, No. 13.

Kunze, et al.. Cone beam reconstruction with displaced flat panel detector, 10th International Meeting on Fully Three-Dimensional Image Reconstruction in Radiology and Nuclear Medicine, 2009, pp. 138-141.

Li et al., Scatter kernel estimation with an edge-spread function method for cone-beam computed tomography imaging Physics in Medicine and Biology, pp. 6729-6748, vol. 51. 2008.

Maslowski, et al., Acuros Cts: A fast, linear Boltzmann transport equation solver for computed tomography scatter-Part I: Core algorithms and validation, Med. Phys., 2018, pp. 1-15.

Ning, et al., X-ray scatter correction algorithm for cone beam CT imaging, Med. Phys., May 2004, pp. 1195-1202, vol. 31, No. 5.

Noo et al., A new scheme for view-dependent data differentiation in fan-beam and cone-beam computed tomography, Physics in Medicine and Biology, 2007, pp. 5593-5414, vol. 52.

Schäfer, et al., FBP and BPF reconstruction methods for circular X-ray tomography with off-center detector, Med. Phys., Jul. 2011, pp. S85-S94, vol. 38, No. 7.

Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.

Siewerdsen, et al., A simple, direct method for x-ray scatter estimation and correction in digital radiography and cone-beam CT, Med. Phys., Jan. 2006, pp. 187-197, vol. 33, No. 1.

Sun, et al., Improved scatter correction using adaptive scatter kernel superposition, Physics in Medicine and Biology, 3ctober2010, pp. 6695-6720, vol. 55.

Tang, et al., A sinogram extrapolation method for CT field of view extension, Proceedings of the Fifth CT Meeting, 2018, pp. 206-209.

Yu, et al.. Radiation dose reduction in computed tomography: techniques and future perspective, Imaging Med., Oct. 2009, pp. 65-84, vol. 1.

Zamyatin, et al.. Helical cone beam CT with an asymmetrical detector, Medical Physics, Oct. 2005, pp. 3117-3127, vol. 32, No. 10.

Zbijewski, et al., Efficient Monte Carlo Based Scatter Artifact Reduction in Cone-Beam Micro-CT, IEEE Transactions an Medical Imaging, Jul. 2006, pp. 817-827, vol. 25, No. 7.

Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.

Zhu, et al. Noise suppression in scatter correction for cone-beam CT, American Association of Physicists in Medicine, 2009, pp. 741-752, vol. 36, No. 3.

Office Action from U.S. Appl. No. 16/694,161 dated Sep. 13, 2021, 18 pages.

* cited by examiner

HELICAL CONE-BEAM COMPUTED TOMOGRAPHY IMAGING WITH AN OFF-CENTERED DETECTOR

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,148, filed Nov. 25, 2019, entitled "APPARATUS AND METHODS FOR SCALABLE FIELD OF VIEW IMAGING USING A MULTI-SOURCE SYSTEM;" Ser. No. 16/694,161, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,192, entitled "MULTI-PASS COMPUTED TOMOGRAPHY SCANS FOR IMPROVED WORKFLOW AND PERFORMANCE;" Ser. No. 16/694,202, filed Nov. 25,2019entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25,2019, entitled "METHOD AND APPARATUS FOR IMPROVING SCATTER ESTIMATION AND CORRECTION IN IMAGING;" and Ser. No. 16/694,230, filed Nov. 25, 2019,entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to computed tomography imaging, and, more particularly, to an apparatus and method for high quality imaging and/or data reconstruction when utilizing an off-centered (offset) detector during cone-beam computed tomography helical scans.

BACKGROUND

Computed tomography (CT) imaging, including cone-beam computed tomography (CBCT), is a valuable tool in radiotherapy. It can be used for patient positioning and dose calculation. It also has the potential to allow physicians to perform adaptive radiotherapy, including in the context of image-guided radiation treatment (IGRT). IGRT can make use of medical imaging technology, such as CT, to collect images of a patient before, during, and/or after treatment.

One popular data acquisition form is a circular scan, with a centered detector for small-object scans (e.g., head), and an off-centered (offset or shifted) detector in the channel direction for large object-scans (e.g., abdomen). For most radiotherapy systems, a circular scan is likely the only practical choice, as the gantry can only rotate in one direction for a limited number of degrees, thus preventing these machines from using a helical source trajectory. A helical scan can provide higher quality images with less artifacts and faster scanning when compared to circular scans, but view completion is much more complex.

BRIEF SUMMARY

In one embodiment, a method of processing projection data from an imaging apparatus utilizing an offset detector includes receiving measured projection data from a current view and at least one conjugate view from the offset detector during a helical imaging scan, determining values of rays missing in the projection data from the current view based on the measured projection data from the at least one conjugate view, and merging the determined values of the missing rays with the measured projection data from the current view to form a completed view of a target.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
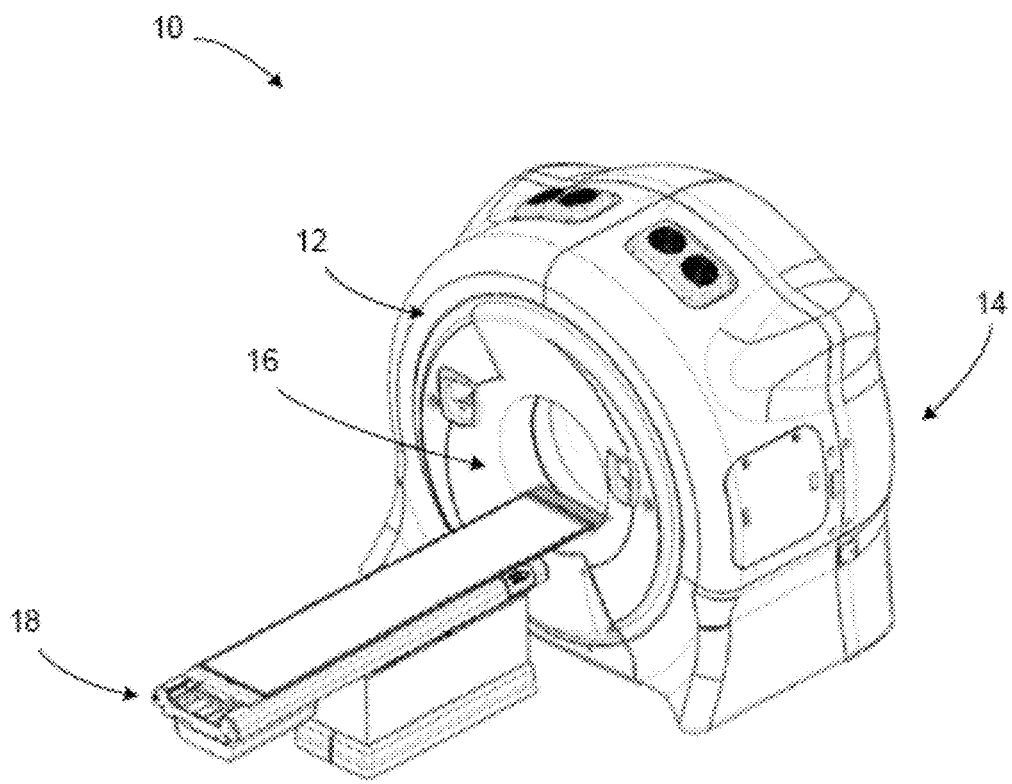
FIG. 1 is a perspective view of an exemplary x-ray imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to high quality imaging and data reconstruction when utilizing an offset detector during CBCT helical scans. In some embodiments, a radiotherapy delivery device and method can make use of an integrated low-energy radiation source for CT for use in conjunction with or as part of IGRT. In particular, for example, a radiotherapy delivery device and method can combine a low-energy collimated radiation source for imaging in a gantry using rotational image acquisition along with a high-energy radiation source for therapeutic treatment. In various embodiments, the low-energy radiation source (e.g., kV) can produce higher quality images than via use of the high-energy radiation source (e.g., MV) for imaging. Images generated with kV energy can have better tissue contrast than with MV energy. High quality volume imaging can be needed for visualization of targets and organs-at-risk (OARS), for adaptive therapy monitoring, and for treatment planning/re-planning. In some embodiments, the kV imaging system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, etc.

In accordance with various embodiments, the x-ray imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

A helical scan trajectory can have several advantages in view of a circular scan. For example, cone-beam artifacts are reduced because a helical scan can provide more complete projection data for image reconstruction. Also, a helical scan can acquire projection data for a large longitudinal coverage with a narrow axial opening, which could substantially reduce scatter contamination in the projection data. Reconstructed images can have significantly improved image quality in terms of low frequency artifacts and result in greatly enhanced soft-tissue contrast. Furthermore, a helical scan can improve scan speed with a large pitch.

Figure 2:
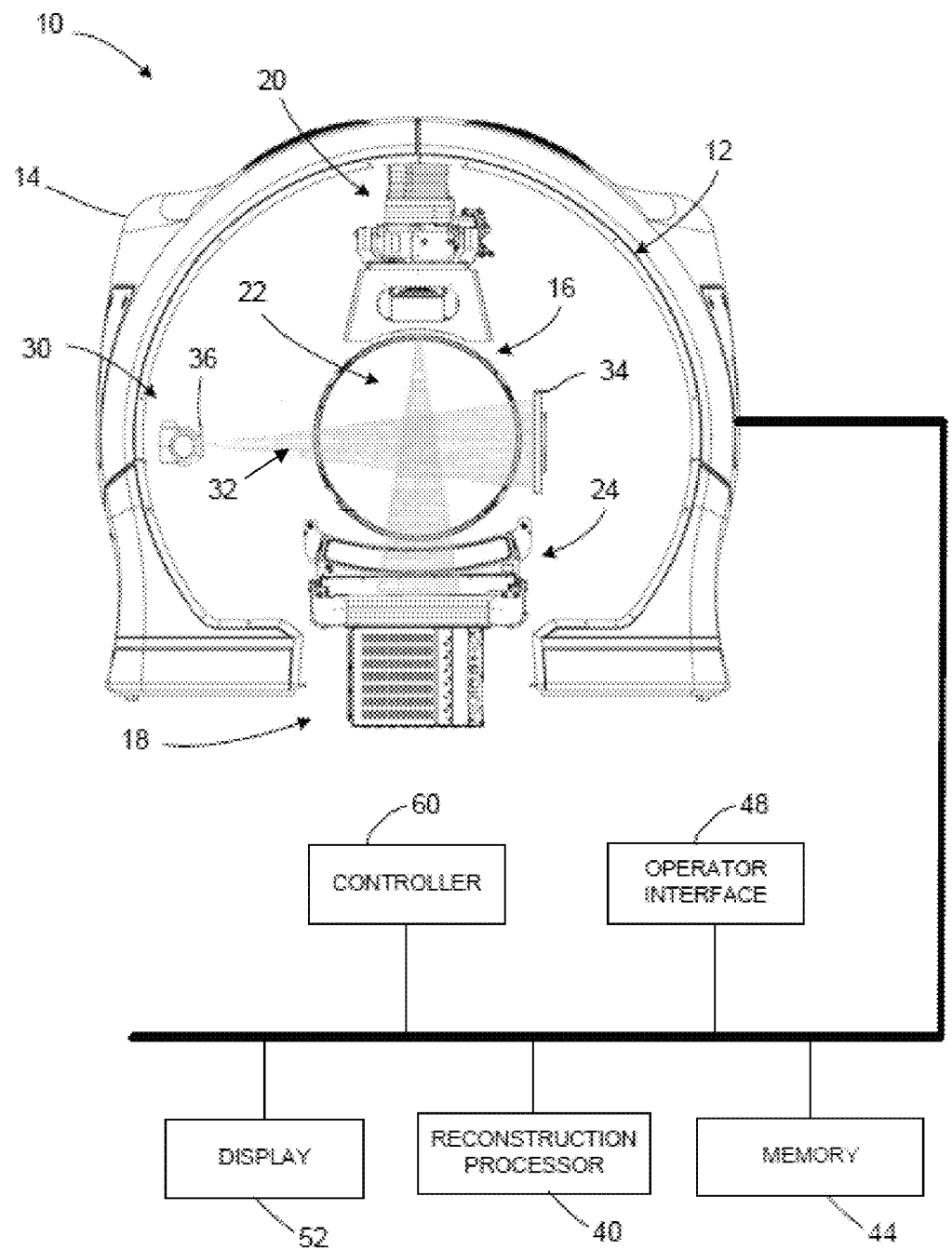
FIG. 2 is a diagrammatic illustration of an x-ray imaging apparatus integrated into an exemplary radiotherapy device in accordance with one aspect of the disclosed technology.

With reference to FIG. 1 and FIG. 2, an x-ray imaging apparatus 10 is shown. It will be appreciated that the x-ray imaging apparatus 10 may be associated with and/or integrated into a radiotherapy device (as shown in FIG. 2) that can be used for a variety of applications, including, but not limited to IGRT. The x-ray imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (e.g., x-ray) and an associated radiation detector while providing sufficient bandwidth for the high-quality imaging data received by the detector. A slip-ring gantry can eliminate gantry rotations in alternating directions in order to wind and unwind cables carrying the power and signals associated with the device. Such a configuration will allow for continuous helical (e.g., fan-beam, cone-beam, etc.) computed tomography, even when integrated into an IGRT system.

A patient support or couch 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. In some embodiments, the patient support can also be moved in a limited range up and down, left and right once it is in the bore 16 to adjust the patient position for optimal treatment.

As shown in FIG. 2, the x-ray imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @ about 70 keV and @ about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the x-ray source 30 rotates around and emits radiation toward the patient.

It will be appreciated that the x-ray detector 34 can take on a number of configurations without departing from the scope of the disclosed technology. As illustrated in FIG. 2, the x-ray detector 34 can be configured as a flat-panel detector (e.g., a multi-row flat panel detector). In accordance with another exemplary embodiment, the x-ray detector 34 can be configured as a curved detector. The detector 34 can be adjusted to an offset (i.e., shifted) position in the channel and/or axial direction.

Although FIGS. 1 and 2 depict an x-ray imaging apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which will be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector 34 (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task being carried out. The beam 32 can be shaped to be various shapes, including, for example, parallelograms. The beamformer 36 can be configured to adjust the shape of the radiation beam 32 by rotation and/or translation of x-ray attenuated material of the beamformer 36.

The collimator/beamformer 36 may be configured in a variety of ways that allow it to adjust the shape of the radiation beam 32 emitted by the x-ray source 30. For example, the collimator 36 can be configured to include a set of jaws or other suitable members that define and selectively adjust the size of an aperture through which the radiation beam from the x-ray source 30 may pass. In accordance with one exemplary configuration, the collimator 36 can include an upper jaw and a lower jaw, where the upper and lower jaws are movable in different directions (e.g., parallel directions) to adjust the size of the aperture through which the radiation beam from the x-ray source 30 passes, and also to adjust the beam position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2, the x-ray imaging apparatus 10 may be integrated with a radiotherapy device that includes a therapeutic radiation source 20 coupled to or otherwise supported by the rotatable gantry 12. In accordance with one embodiment, the therapeutic radiation source 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation. In one embodiment, the first source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the first source of radiation 20 has a higher energy level (peak and/or average, etc.) than the second source of radiation 30.

In one embodiment, the therapeutic radiation source 20 is a linear accelerator (LINAC) producing therapeutic radiation (e.g., MV source) and the imaging system comprises an independent x-ray imaging source of radiation producing relatively low intensity and lower energy imaging radiation (e.g., kV source). In other embodiments, the therapeutic radiation source 20 could be a radioisotope, such as, for example, Co-60, and it can generally have energy >1 MeV. The therapeutic radiation source 20 can emit one or more beams of radiation (indicated generally by 22) toward a region-of-interest (ROI) within a patient supported on the patient support 18 in accordance with a treatment plan. Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a collimator. The collimator associated with the therapeutic radiation source 20 can be configured in a number of ways, similar to the collimator/beamformer 36 associated with the imaging source 30. For example, a collimator/beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, x-ray imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and/or any information obtained from these or other imaging modalities. In some embodiments, the x-ray imaging apparatus 10 can track in-treatment patient, target, or ROI motion.

A reconstruction processor 40 can be operatively coupled to detector 24 and/or x-ray detector 34. In one embodiment, the reconstruction processor 40 is configured to generate patient images based on radiation received by the x-ray detector 34 from the x-ray source 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The x-ray imaging apparatus 10 can include an operator/user interface 48, where an operator of the x-ray imaging apparatus 10 can interact with or otherwise control the x-ray imaging apparatus 10 to provide input relating to scan or imaging parameters and the like. The operator interface 48 can include any suitable input devices, such as a keyboard, mouse, voice-activated controller, or the like. The x-ray imaging apparatus 10 can also include a display 52 or other human-readable element to provide output to the operator of the x-ray imaging apparatus 10. For example, the display 52 can allow the operator to observe reconstructed patient images and other information, such as imaging or scan parameters, related to operation of the x-ray imaging apparatus 10.

As shown in FIG. 2, the x-ray imaging apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer 36 controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an x-ray imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an x-ray imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with x-ray imaging apparatus 10.

X-ray imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented.

It will be appreciated that the x-ray source 30 and the x-ray detector 34 can be configured to provide rotation around the patient during an imaging scan in a number of ways. In one embodiment, synchronizing the motion and exposure of the x-ray source 30 with the longitudinal motion of the patient support 18 can provide a continuous helical acquisition of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of radiotherapy devices 10 described above.

In one embodiment, the gantry 12 rotation speed, the patient support 18 speed, the beamformer 36 shape, and/or the detector 34 readout could all be constant during image acquisition. In other embodiments, one or more of these variables could change dynamically during image acquisition. The gantry 12 rotation speed, patient support 18 speed, beamformer 36 shape, and/or detector 34 readout can be varied to balance different factors, including, for example, image quality and image acquisition time.

In other embodiments, these features can be combined with one or more other image-based activities or procedures, including, for example, patient set up, adaptive therapy monitoring, treatment planning, etc.

In several embodiments, CBCT uses an x-ray source 30 with a flat panel detector 34 as an imaging modality for radiotherapy. Due to the limited transverse panel size of typical detectors, a detector shift in the channel direction is usually implemented for a larger field-of-view (FOV). Such a detector 34 displacement (offset) is common for circular CBCT scans and can pose significant difficulty in image reconstruction, as the projection data acquired from such setup are consequently truncated in both the axial and transverse directions.

CBCT with a helical trajectory can be a better imaging tool for radiotherapy and IGRT in view of the benefits over circular scans mentioned above. However, an offset detector 34, for an enlarged FOV, results in an even more complex and difficult reconstruction problem when compared to the circular trajectory. Known techniques may lose key properties after view completion and filtration using data acquired by an offset detector during a helical scan. For example, for an axially invariant object, the exactness property of the Feldkamp, Davis, and Kress (FDK) framework does not hold anymore in this situation.

In various embodiments, described below is a new view completion and image reconstruction framework for helical cone-beam scans with an offset flat panel detector using a general cone beam filtered-back projection-based (CBFBP) framework. This reconstruction framework is not only computationally efficient, but is also exact if the object is invariant in the axial direction. Furthermore, this reconstruction framework can be more accurate in applications where the object is nearly axial invariant.

Convention

The following notation is used in the following embodiments. A scalar is denoted by a lower-case letter, and a vector or vector position (e.g., 2D or 3D) is denoted by a lower-case letter with an underscore. In particular, the letter e with an underscore, i.e., e, is a unit vector. Let [x, y, z] be the coordinates of the world coordinate system, then the unit vectors of the x-, y-, and z-axes can be expressed as $e_x$, $e_y$, and $e_z$, respectively. In this case, a 3D vector x with coordinates $[x, y, z]^T$ can be expressed as $x=[x, y, z]^T$. T stands for transpose. If not specified otherwise, a lower-case letter with a hat indicates the value is estimated, whereas a lower-case letter with a bar indicates the value is from a conjugate ray.

The scanned object (e.g., patient, target) is compact, and the compact space is denoted by $\Omega$. The attenuation coefficient of the object at vector location x is denoted by f(x), whereas its reconstruction is denoted by $\hat{f}(x)$. The x-ray source 30 rotates around the iso-center, and the view angle is denoted by $\lambda$. Therefore, the spatial location of the source 30 is fully characterized by the view angle, and we denote its vector position by a ($\lambda$). The source-to-isocenter distance is denoted as R, and the source-to-detector distance as D. The x-ray detector 34 is an exemplary flat panel detector, and the 2D panel is spanned by the basis vectors $e_u$ and $e_v$, with $e_u$ for the channel direction and $e_v$ for the row direction. The coordinates of a point in the detector plane are expressed as [u, v]. The exemplary detector cells are rectangle and of the same size. The cell width and height are denoted by $\Delta u$ and $\Delta v$, respectively. The measured value on the detector 34 after the log operation (i.e., line integral) is denoted by g($\lambda$, u, v).

Figure 3:
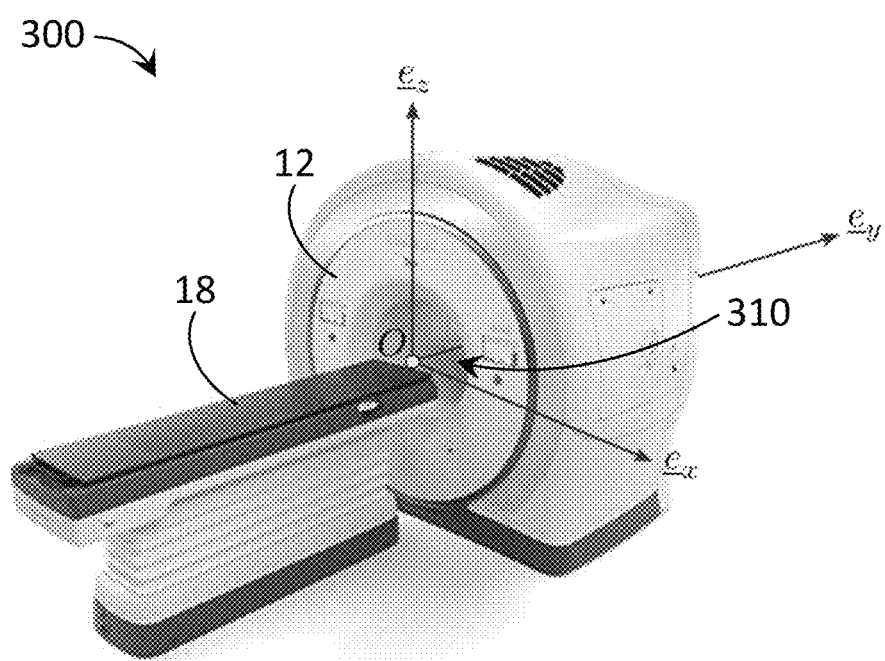
FIG. 3 is an illustration of an exemplary x-ray imaging apparatus shown with a world coordinate system defined.

With reference to FIG. 3, an illustration 300 of an x-ray imaging apparatus is shown with a world coordinate system 310 defined. The origin, denoted as O, is the iso-center of the gantry 12 and the unit vectors associated with the x-, y-, and z-axes are shown as $e_x$, $e_y$, and $e_z$, respectively. Viewing from the front of the gantry 12, the x-axis $e_x$ is horizontal and points to the right, the y-axis $e_y$ points into the gantry plane, and the z-axis $e_z$ is vertical and points to the top. The x-, y-, and z-axes follow the right-hand rule.

Figure 4:
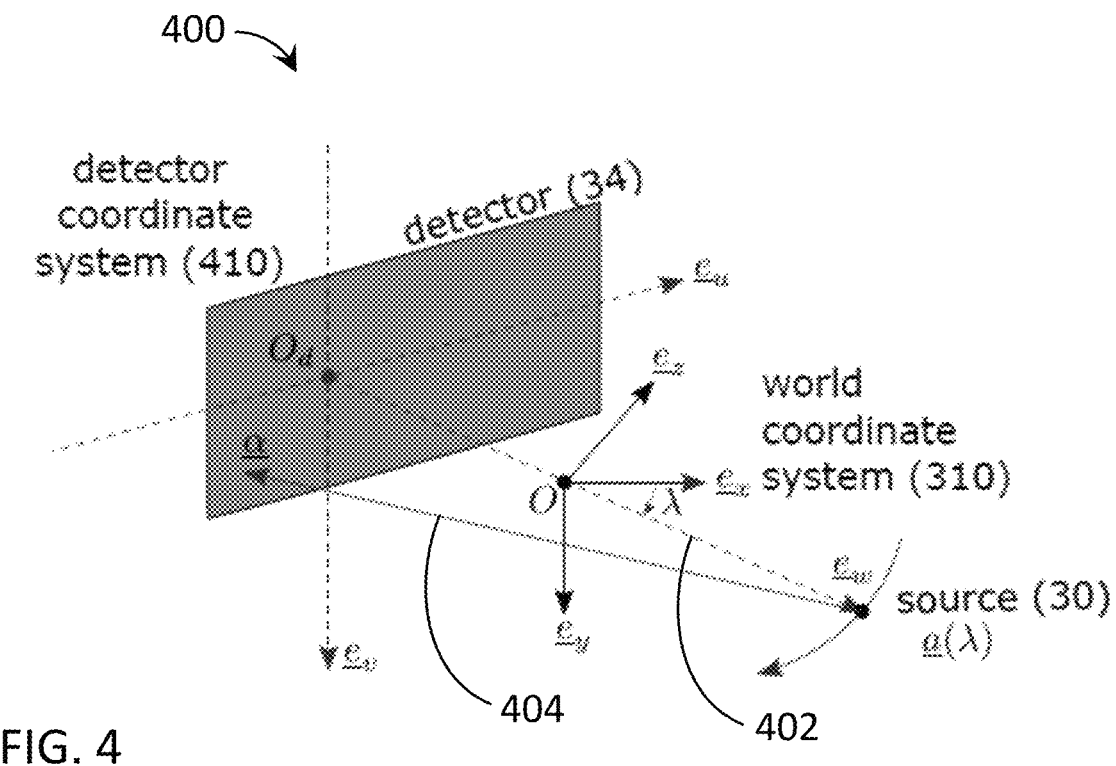
FIG. 4 is an illustration of the 3D geometry of an exemplary data acquisition system.
Figure 5:
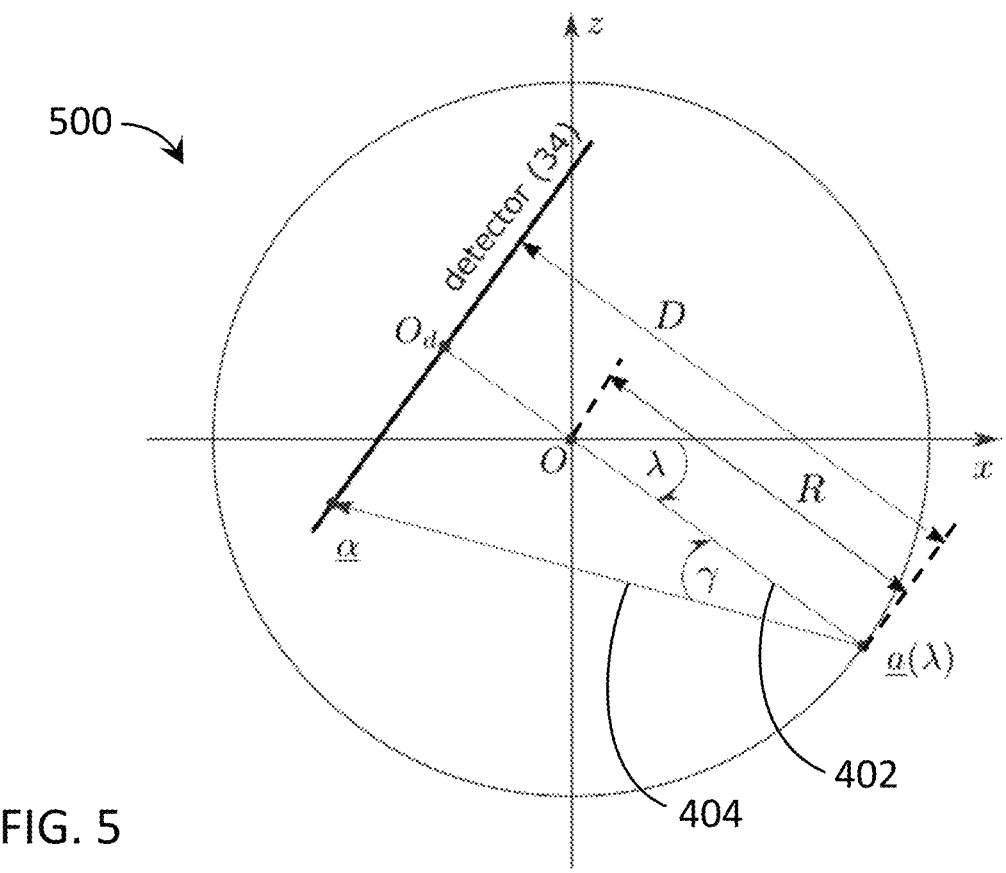
FIG. 5 is an illustration of the geometry of a data acquisition system in an exemplary (x, z)-plane.

In an exemplary embodiment, the x-ray source 30 rotates clockwise when viewing from the front of the gantry 12. FIG. 4 shows an illustration 400 of the 3D geometry of an exemplary data acquisition system. FIG. 5 shows an illustration 500 of the geometry of the data acquisition system in an exemplary (x, z)-plane. The view angle, $\lambda$, is defined as the angular distance from the x-axis $e_x$ to the virtual line 402 connecting the source 30 and the rotation axis in a clockwise fashion when looking from the front of the gantry 12, with its 3D vector position denoted as a ($\lambda$). The rotation axis is along the world coordinate y-axis $e_y$. The detector 34 is positioned such that it is perpendicular to the plane defined by the source 30 and the rotation axis, its channels are parallel to the rotation axis, and its rows are perpendicular to the rotation axis. The piercing point of line 402 connecting the source 30 and the iso-center O at the detector 34 is defined as the origin of a detector coordinate system 410, which is denoted by $O_d$.

As shown in FIG. 4, two coordinate systems are involved with the exemplary data acquisition system. In particular, the data acquisition makes reference to the world coordinate system 310 with origin at O and the detector coordinate system 410 with origin at $O_d$. As introduced above, the detector coordinate system 410 is defined by basis vectors $e_u$ (in the channel direction), $e_v$ (in the row direction) in the detector 34 plane, and $e_w$ (perpendicular to the detector 34 plane and pointing from $O_d$ to a). Here, $O_d$ is defined as the piercing point on the detector 34 of the line 402 connecting the source 30 (with vector position a ($\lambda$)) and O extended to the detector 34, along $e_w$. Whereas $\alpha(\lambda, u, v)$ is a unit vector 404 pointing from the source 30 vector position a ($\lambda$) to the detector 34 cell located at coordinates [u, v] in the detector coordinate system 410.

FIG. 5 illustrates the geometry 500 of the data acquisition system in an exemplary (x, z)-plane. Here, R is the source-to-iso distance, D is the source-to-detector distance, $\lambda$ is the view angle, and $\gamma$ is the fan angle.

The detector coordinate system 410 is spanned by basis vectors $e_v(\lambda)$, $e_u(\lambda)$, and $e_w(\lambda)$. They are shown in FIG. 4 and defined in equation 1:

$$e_v(\lambda)=[0,1,0]^T$$

$$e_u(\lambda)=[\sin(\lambda),0, \cos(\lambda)]^T$$

$$e_w(\lambda)=[\cos(\lambda),0, -\sin(\lambda)]^T \quad (1)$$

An x-ray (from the source 30) measured at the detector 34 is denoted by $\mathcal{L}$ ($\lambda$, u, v), and the unit vector of such a ray pointing from source a ($\lambda$) to a detector position (u, v) is denoted by $\alpha(\lambda, u, v)$, with reference to FIGS. 4 and 5. By construction, this unit vector $\alpha(\lambda, u, v)$ can be obtained using equation 2:

$$\underline{\alpha} = (\lambda, u, v) = \frac{ue_u(\lambda) + ve_v(\lambda) - De_w(\lambda)}{\sqrt{D^2 + u^2 + v^2}} \quad (2)$$

Using the above notation, a line integral along an x-ray can be expressed according to equation 3:

$$g(\lambda,u,v)=\int_0^{+\infty} f(a(\lambda)+t\underline{\alpha})dt, \quad (3)$$

The angle between $\mathcal{L}$ and the central plane defined by a ($\lambda$) and the rotation axis is called the fan angle and is denoted by $\gamma$, as shown in FIG. 5. The fan angle $\gamma$ is of the same sign as u, and is defined by equation 4:

$$\gamma = \arctan\left(\frac{u}{D}\right) \quad (4)$$

A helical trajectory is implemented by a combination of gantry 12 rotation and patient support/couch 18 translation. The gantry 12 rotation is defined above. The couch 18 direction is denoted by cdir. In one embodiment, the default direction of the couch 18 is into the gantry 12 and cdir is defined as 1. In another embodiment, where the couch 18 is moving out of the gantry 12, cdir is set to be −1. Note that longitudinal movement of the source 30 is relatively opposite to the longitudinal movement of the couch 18. If both the gantry 12 rotation speed and couch 18 movement speed are constant, then the source 30 trajectory can be fully characterized by view angle $\lambda$. Let $\lambda_s$ and $h_s$ be the starting view angle and the starting y position of the trajectory, respectively. Let $H_p$ be the longitudinal distance travelled by the source 30 relative to the couch 18 per rotation. Note that $H_p$ is positive when cdir is −1 and negative when cdir is 1. Let the detector 34 height (in v) be $H_{iso}$ at iso-center. The normalized helical pitch is denoted by p according to equation 5:

$$p = \left|\frac{H_p}{H_{iso}}\right| \quad (5)$$

The helical trajectory then can be described by equation 6:

$$a(\lambda)=[R \cos \lambda, h(\lambda), -R \sin \lambda]^T,$$

where $h(\lambda)=H_p(\lambda-\lambda_s)/2\pi+h_s$. $\quad (6)$

Figure 6:
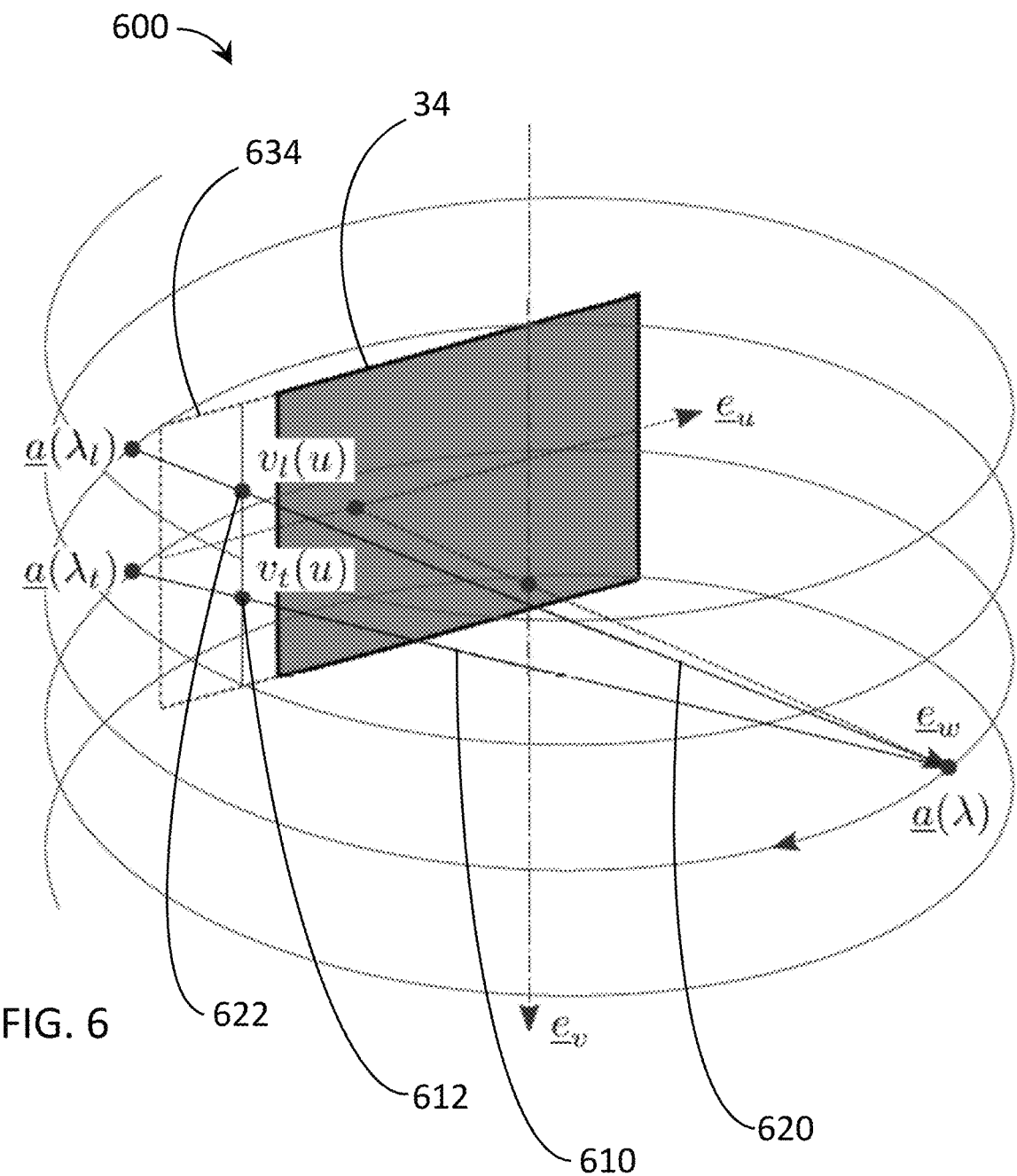
FIG. 6 is a 3D illustration of an exemplary configuration for a helical trajectory with an offset detector and conjugate views for view completion.

FIG. 6 is a 3D illustration 600 of an exemplary configuration for the helical trajectory with an offset detector 34 and conjugate views for view completion. In this embodiment, and with additional reference to FIGS. 3 and 4, the patient couch 18 is moving into the gantry (i.e., cdir=1), and the relative source 30 longitudinal moving direction is toward the negative y-axis $e_y$. Therefore, the leading edge of the detector 34 is toward the front of the gantry 12 ($-e_y$) and the trailing (tail) edge of the detector 34 is toward the back ($e_y$). Here, letters "l" and "t" refer to leading and trailing, respectively. A detector plane 634 defined by the detector 34 is also shown. Conjugate views at $\lambda_l$ and $\lambda_t$, as well as Tam-Danielsson window curves $v_l$ and $v_t$, are shown in FIG. 6 and will be discussed in detail below.

Below is a table summarizing the definitions of variables and exemplary simulation values used in exemplary embodiments:

TABLE I

Definition of Variables

| Variables | Meaning | Value |
|---|---|---|
| $[e_x, e_y, e_z]$ | basis of the 3D world coordinate system | n.a. |
| $[e_v, e_u, e_w]$ | basis of the 3D detector coordinate system | n.a. |
| $[e_m, e_n]$ | basis of the 2D slab coordinate system | n.a. |
| $[\Delta u, \Delta v]$ | detector physical cell size in u and v | [0.45, 0.45] mm for simulation |
| $\gamma$ | fan angle | defined by Eq 4 |
| $\lambda$ | view angle | n.a. |
| $\lambda_s$ | starting view angle | n.a. |
| $\alpha$ | unit vector pointing from source to detector | defined by Eq 2 |
| R | source-to-iso distance | 1080 mm for simulation |
| D | source-to-detector distance | 1620 mm for simulation |
| H | Detector height(physical) | 432 mm for 4343 |
| $H_p$ | source longitudinal translation per rotation | depending on pitch |
| $H_l$ | Detector height on the lead side | n.d. |
| $H_t$ | Detector height on the tail side | n.d. |
| $H_{iso}$ | Detector height normalized at iso-center | $H_{iso}$ = R * H/D |
| p | normalized helical pitch (always positive) | n.d. |
| h | source position in y | a function of lambda and pitch |
| $h_s$ | starting y position of the x-ray source | n.d. |
| $\bar{u}$ | u coordinate of the conjugate view | n.d. |
| $\lambda_l$ | view angle of the conjugate view on the leading side | n.d. |
| $\lambda_t$ | view angle of the conjugate view on the tail side | n.d. |
| cdir | couch direction | 1 into gantry; −1 out |
| $g(\lambda, u, v)$ | line integral along $\mathcal{L}$ (λ, u, v) | defined by Eq 3 |

Framework

As mentioned above, the attenuation coefficient of the object at vector location x is denoted by f(x), whereas its reconstruction is denoted by f̂(x). With use of the conventions described above, a reconstruction framework for a CBCT helical scan using an offset detector is based on equations 7 and 8:

$$\hat{f}(\underline{x}) = \int_{\Lambda(\underline{x})} d\lambda \frac{1}{(a(\lambda) - \underline{x}) \cdot e_w} w(\lambda, \underline{x}) g_H(\lambda, u^*, v^*), \text{ where} \quad (7)$$

$$u^*(\lambda, \underline{x}) = -\frac{D(\underline{x} - a(\lambda)) \cdot e_u}{(\underline{x} - a(\lambda)) \cdot e_w} \quad (8)$$

$$v^*(\lambda, \underline{x}) = -\frac{D(\underline{x} - a(\lambda)) \cdot e_v}{(\underline{x} - a(\lambda)) \cdot e_w}$$

The term $g_H$ in equation 7 is defined according to equation 9:

$$g_H(\lambda, u, v) = h_H^\Delta(u) * g'_{CB}(\lambda, u, v), \quad (9)$$

with $h_H^\Delta(u)$ being an apodized Hilbert transform, and according to equation 10:

$$g'_{CB}(\lambda, u, v) = \frac{D}{\sqrt{D^2 + u^2 + v^2}} \left.\frac{\partial \hat{g}(\lambda, u, v)}{\partial \lambda}\right|_{\alpha\,fixed}, \quad (10)$$

where ĝ(λ, u, v) is the projection data feed into the reconstruction engine, and α(λ, u, v) is the unit vector pointing from the source a(λ) to the detector 34 point (u, v).

The term w(λ, x) in equation 7 is the aperture weighting function that addresses data redundancy during back-projection. It is defined by equation 11:

$$w(\lambda, \underline{x}) = \frac{w_u(u^*)w_v(v^*)}{\sum_{(u,v)\in\Phi(\lambda,\underline{x})} w_u(u)w_v(v)}, \quad (11)$$

where (u*, v*) are defined in Equation 8, $w_u$ and $w_v$ are channel and row weighting functions, and Φ(λ, x) is the set of all measured or estimated rays that: i) go through point x; and ii) belong to the plane going through a(λ) and parallel to $e_y$.

This reconstruction (f̂(x)) can be utilized by a framework that accounts for a source 30 following a helical scan trajectory with an offset detector 34, as described above.

The included flow charts and block diagrams illustrate exemplary configurations and methodologies associated with features of a reconstruction framework in accordance with the systems described herein. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 7:
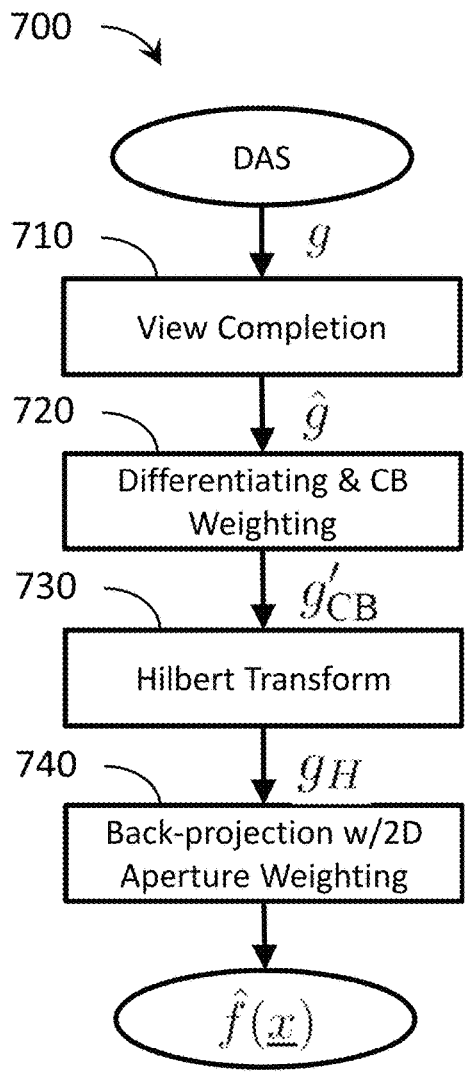
FIG. 7 is a flow chart of an exemplary reconstruction framework.

FIG. 7 is a flow chart of an exemplary reconstruction framework 700. Framework 700 can be applied to a CBCT helical scan using an offset detector, as described above. In this embodiment, at step 710, the framework 700 completes views as necessary due to the limited FOV created by the offset detector, based on data received from the data acquisition system (DAS). In particular, the data received from the DAS includes calibrated projection data g (x-ray line integrals g(λ, u, v)), as specified above in equation 3. The view completion step 710 will be described in more detail below.

After view completion in step 710, the projection data feed ĝ(λ, u, v) is provided to the reconstruction engine. At step 720, the framework 700 applies differentiating and cone beam (CB) weighting to the projection data feed ĝ(λ, u, v) to generate g'$_{CB}$(λ, u, v), according to equation 10 above. At step 730, the framework 700 applies a Hilbert transform to g'$_{CB}$(λ, u, v) to generate $g_H$(λ, u, v), according to equation 9 above. At step 740, the framework 700 applies a back-projection with 2D aperture weighting to $g_H$(λ, u, v) to generate reconstruction images (f̂(x)), according to equation 7 above. More detail is provided below.

Returning to the view completion step 710, because the detector 34 is offset (shifted), a view completion process 710 has to be performed before data can be fed into equation 10 at step 720. The detector 34 is offset, for example, for an enlarged FOV. For simplicity, the description herein refers to the detector 34 as always shifted in the direction of $e_u(\lambda)$. However, in other embodiments, the detector 34 can be shifted in any transverse and/or axial direction with similar treatment.

For conciseness, the view-completion algorithm is described using the geometry described in the embodiment shown in FIG. 6. Allowing for two couch 18 motions, one can be moving into the gantry 12 (i.e., cdir=1) and the other can be moving out of the gantry 12 (i.e., cdir=−1).

A slab plane is defined by the source current view $a(\lambda)$ and a detector column located at u, and is denoted by $\Pi(\lambda, u)$. This plane intersects the previous (trailing) and next (leading) rotations of the source trajectory at two view angles, which are denoted by $\lambda_t$ and $\lambda_l$, respectively. The detector plane 634 is the plane of detector 34, which includes a virtual extension into the area behind the scanned object vacated by offsetting the detector 34 (i.e., an area no longer directly measured by detector 34 in the current view). Line 610 connects $a(\lambda)$ and $a(\lambda_t)$ and intersects the detector plane 634 at point 612 [u, $v_t$] (labeled as $v_t(u)$). Line 620 connects $a(\lambda)$ and $a(\lambda_l)$ and intersects the detector plane 634 at point 622 [u, $v_l$] (labeled as $v_l(u)$). Note that the v coordinates $v_t$ and $v_l$ are on the Tam-Danielsson window curves. These curves can be obtained using the following equations in 12:

$$v_l(u) = \frac{D(2\gamma + \pi)}{R(1 - \cos(2\gamma + \pi))} \frac{H_p}{2\pi} \quad (12)$$
$$v_t(u) = \frac{D(2\gamma - \pi)}{R(1 - \cos(2\gamma - \pi))} \frac{H_p}{2\pi}$$

where $\gamma$ is the fan angle defined by u and can be calculated by equation 4. When the couch 18 is moving into the gantry 12 (i.e., cdir=1), $H_p$ is negative, and $v_l(u)$ of the Tam-Danielsson window corresponding to the leading edge is negative, whereas $v_t(u)$ of the Tam-Danielsson window corresponding to the trailing edge is positive.

The purpose of view completion step 710 is to assess or evaluate the missing rays (e.g., in the enlarged FOV due to the offset detector 34) using measurements from conjugate rays from neighboring rotations in the same slab plane to determine or calculate the missing data. "Missing rays" refers to the rays that would have passed from the source 30 through the object and been measured by the detector 34 but were not available because the detector 34 was shifted for the larger FOV. The missing rays occur in the area shown in FIG. 6 as the dotted line portion of the detector plane 634. These rays and their data are necessary to complete the view of the object from the current view $a(\lambda)$. The data associated with these rays can be estimated or determined from conjugate rays. "Conjugate rays" refers to the rays from views located on the opposite side that are used to assess the missing rays. In one technique, the view completion process would be pixel dependent such that conjugate rays used for determining the missing rays go through the same pixel that is going to be back-projected. However, such a shift variant scheme would dramatically increase computational cost. In another embodiment, the scheme is shift invariant so that the parameters used for missing ray assessment can be pre-calculated.

Figure 8:
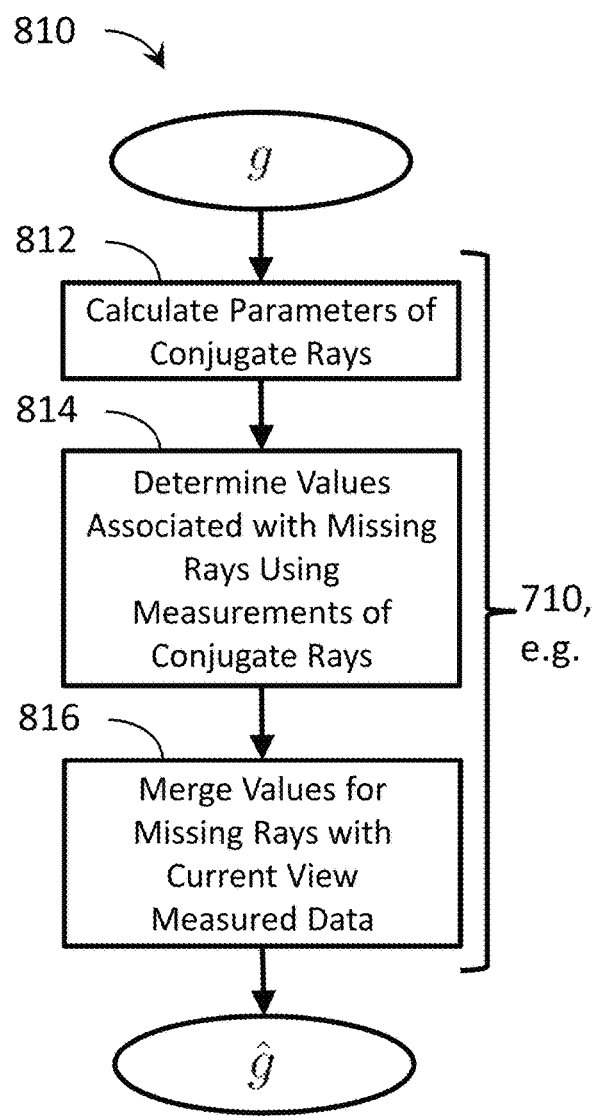
FIG. 8 is a flow chart of an exemplary view completion method.

For example, FIG. 8 is a flow chart of an exemplary view completion method 810. In one embodiment, reconstruction framework 700's view completion step 710 comprises view completion method 810. In this embodiment, at step 812, the method 810 calculates defining parameters of the conjugate rays needed to determine values for the missing rays. In particular, step 812 calculates the u coordinate of the conjugate rays, denoted by $\bar{u}$, and the view angles of the conjugate trailing and leading rays, $\lambda_t$ and $\lambda_l$, respectively. By construction, these values can be calculated according to the equations in 13:

$$\bar{u} = -u$$
$$\lambda_t = \lambda + 2\gamma - \pi$$
$$\lambda_l = \lambda + 2\gamma + \pi \quad (13)$$

Figure 9:
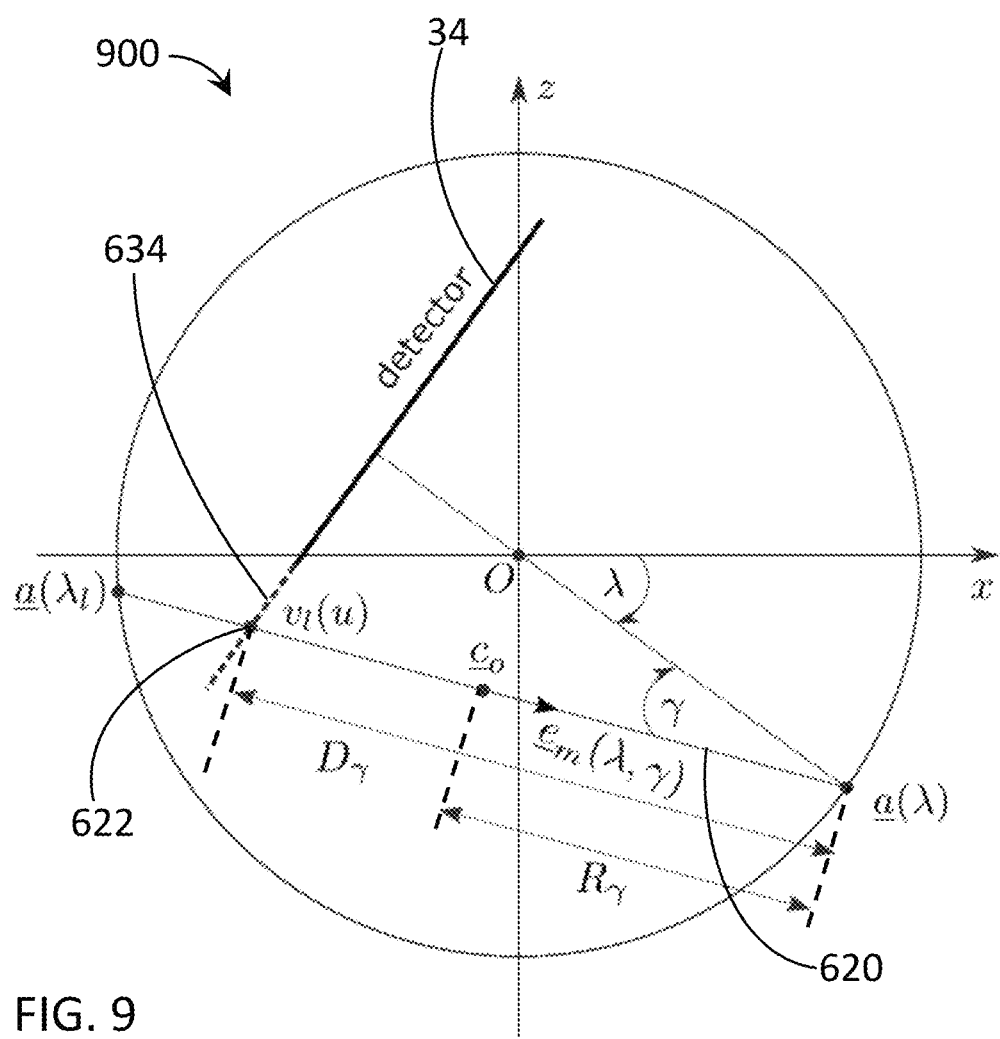
FIG. 9 is an illustration of an exemplary geometry of a helical data acquisition system in an (x, z)-plane.

Next, at step 814, the method 810 determines values associated with the missing rays using measurements of the conjugate rays. FIG. 9 illustrates the exemplary geometry 800 of a helical data acquisition system in an (x, z)-plane. With additional reference to FIG. 6, the (m, n) 2D coordinate system is introduced for the slab plane $\Pi(\lambda, u)$. The basis vectors are denoted by $e_m$ and $e_n$, with $e_m$ parallel to the (x, z)-plane, and $e_n$ parallel to the rotation axis pointing in the same direction as the longitudinal source motion. These two basis vectors $e_m$, $e_n$ are defined by equation 14:

$$e_m(\lambda, u) = \cos\gamma\, e_w(\lambda) - \sin\gamma\, e_u(\lambda)$$
$$e_n(cdir) = -cdir\, e_v \quad (14)$$

where $e_v$, $e_u$, and $e_w$ are defined in equation 1. The origin of the (m, n)-plane is denoted as $c_o$, whose world coordinates can be calculated according to equation 15:

$$c_o(\lambda, u) = a(\lambda) - R_\gamma e_m(\lambda, u), \quad (15)$$

where $e_m$ is defined in equation 14 and $R\gamma$ is defined by equation 16:

$$R\gamma = R\cos\gamma \quad (16)$$

Similar to $R\gamma$, $D\gamma$ is defined according to equation 17:

$$D_\gamma = \frac{D}{\cos\gamma}. \quad (17)$$

In addition, other variables are related to the slab plane $\Pi(\lambda, u)$. These variables in (m, n)-coordinates are discussed below in relation to FIGS. 11-14 and are summarized in Table II:

TABLE II

| | Variable Definitions in the (m, n)-Plane | |
|---|---|---|
| Variables | Definition | (m, n) coordinates |
| $a(\lambda_l)$ | leading conjugate view | $[-R_\gamma, (2\gamma + \pi)H_p/\pi]$ |
| $a(\lambda_t)$ | tail conjugate view | $[-R_\gamma, (2\gamma - \pi)H_p/\pi]$ |
| $a(\lambda)$ | current view | $[R_\gamma, 0]$ |

TABLE II-continued

Variable Definitions in the (m, n)-Plane

| Variables | Definition | (m, n) coordinates |
| --- | --- | --- |
| $c_l$ | Intersection of the line connecting $a(\lambda)$ and $a(\lambda_l)$ at the n-axis | $[0, (2\gamma + \pi)H_p/(2\pi)]$ |
| $c_t$ | Intersection of the line connecting $a(\lambda)$ and $a(\lambda_t)$ at the n-axis | $[0, (2\gamma - \pi)H_p/(2\pi)]$ |
| $c_o$ | Origin of the (m, n) coordinate system | $[0, 0]$ |
| d(u, v) | The detector cell of the current view at [u, v] | $[R_\gamma - D_\gamma, -cdir * v]$ |
| s | Intersection between the line connecting $a(\lambda_l)$ and the bottom edge of the detector (at view $\lambda_l$) and the line connecting $a(\lambda_t)$ and the top edge of the detector (at view $\lambda_t$) | [ms, ns] defined in Equation 18 |
| $b_l$ | Intersection between the line connecting $a(\lambda)$ and $a(\lambda_l)$ the line connecting $a(\lambda_t)$ and s | $\zeta(a(\lambda_l), a(\lambda), a(\lambda_t), s)$ |
| $b_t$ | Intersection between the line connecting $a(\lambda)$ and $a(\lambda_t)$ and the line connecting $a(\lambda_l)$ and s | $\zeta(a(\lambda_t), a(\lambda), a(\lambda_l), s)$ |
| $H_l$ | Physical detector height above the m-axis at the current view $a(\lambda)$ | n.a. |
| $H_t$ | Physical detector height below the m-axis at the current view $a(\lambda)$ | n.a. |

The [ms, ns] coordinates listed in Table II are defined in equation 18:

$$ms = \frac{|H_p|}{|H_l| + |H_t|} D_\gamma - R_\gamma \quad (18)$$

$$ns = \left(\frac{\pi + 2\gamma}{2\pi} - \frac{|H_t|}{|H_t| + |H_l|}\right)|H_p|$$

The disclosure below will also make use of an exemplary function to calculate the intersection of two lines that are defined by four co-planer points. Let the first line, denoted by $\mathcal{L}_1(a, b)$, be defined by a and b, and let the second line, denoted by $\mathcal{L}_2(c, d)$, be defined by c and d. Assuming $a \neq b$ and $c \neq d$ and that the two lines are not parallel:

$$(d-c) \cdot (b-a)^\perp \neq 0,$$

where operator $\perp$ refers to a 90 degree counter-clockwise rotation of a vector. Let the intersection between $\mathcal{L}_1(a, b)$ and $\mathcal{L}_2(c, d)$ be x. Then x can be obtained by the function $\zeta(a, b, c, d)$, which is mathematically defined as:

$$\underline{x} = \zeta(\underline{a}, \underline{b}, \underline{c}, \underline{d}) = \frac{(\underline{a} - \underline{c}) \cdot (\underline{b} - \underline{a})^\perp}{(\underline{d} - \underline{c}) \cdot (\underline{b} - \underline{a})^\perp}(\underline{d} - \underline{c}) + \underline{c}.$$

Referring back to method 810, step 814 determines the values associated with the missing rays using measurements from the conjugate rays. In an exemplary embodiment, step 814 of the view completion process can be implemented in several steps.

Figure 10:
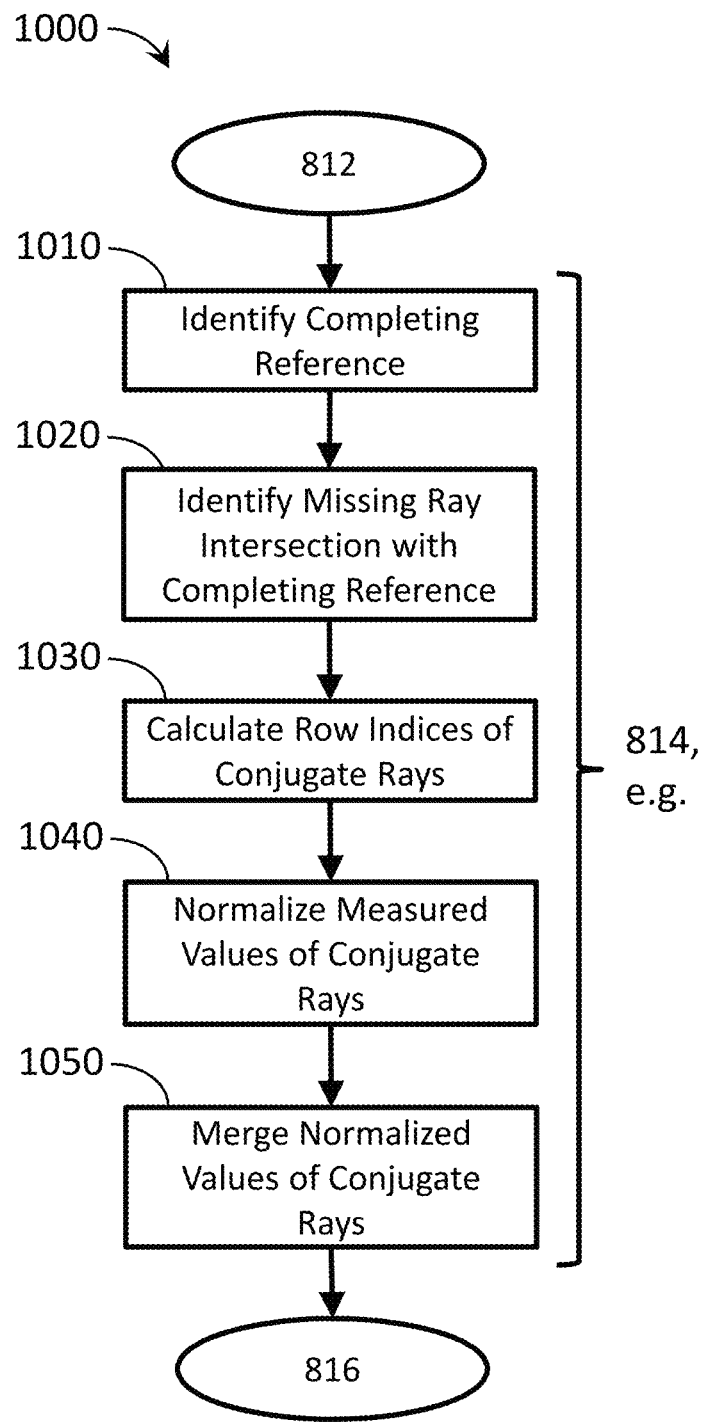
FIG. 10 is a flow chart of an exemplary method for determining the values of the missing rays.

For example, FIG. 10 is a flow chart of an exemplary method 1000 for determining the values of the missing rays. In one embodiment, view completion method 810's step 814 comprises method 1000. In this embodiment, at step 1010, the method 1000 identifies the completing reference, which consists of: i) the portion of the n-axis above $c_l$; ii) the line segment between $b_l$ and $b_t$; and iii) the portion of the n-axis below $c_t$. For a fixed source-detector configuration, different pitches will result in different data availability for the view completion process. Note that s moves along a horizontal line (i.e., parallel to $e_m$) when the pitch varies. Once $b_l$ and $b_t$ are calculated, the following extra procedure to unify the aforementioned two cases of pitch values can be performed.

Figure 11:
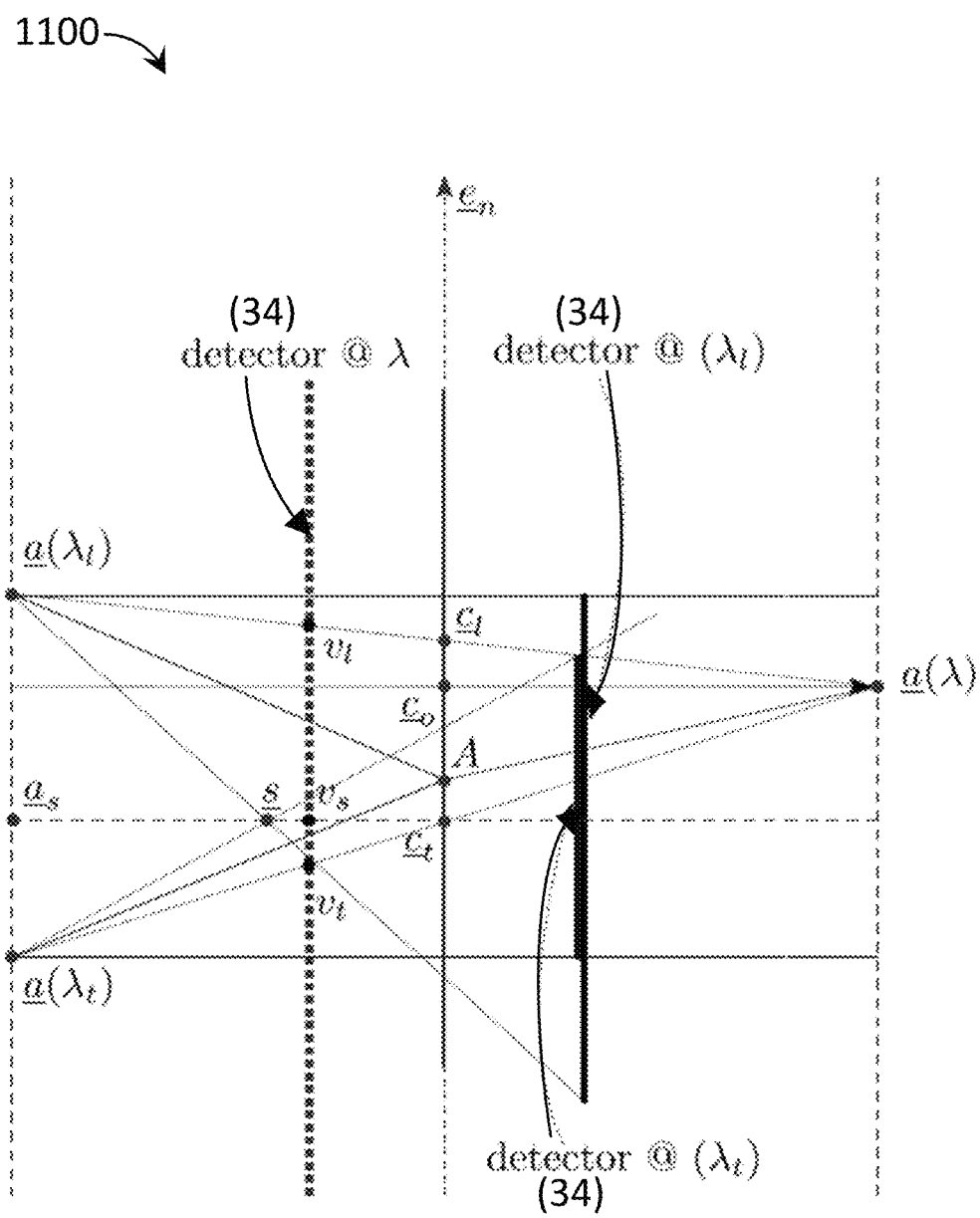
FIG. 11 is an illustration of an exemplary geometry of a small pitch helical data acquisition in an (m, n) coordinate system.
Figure 12:
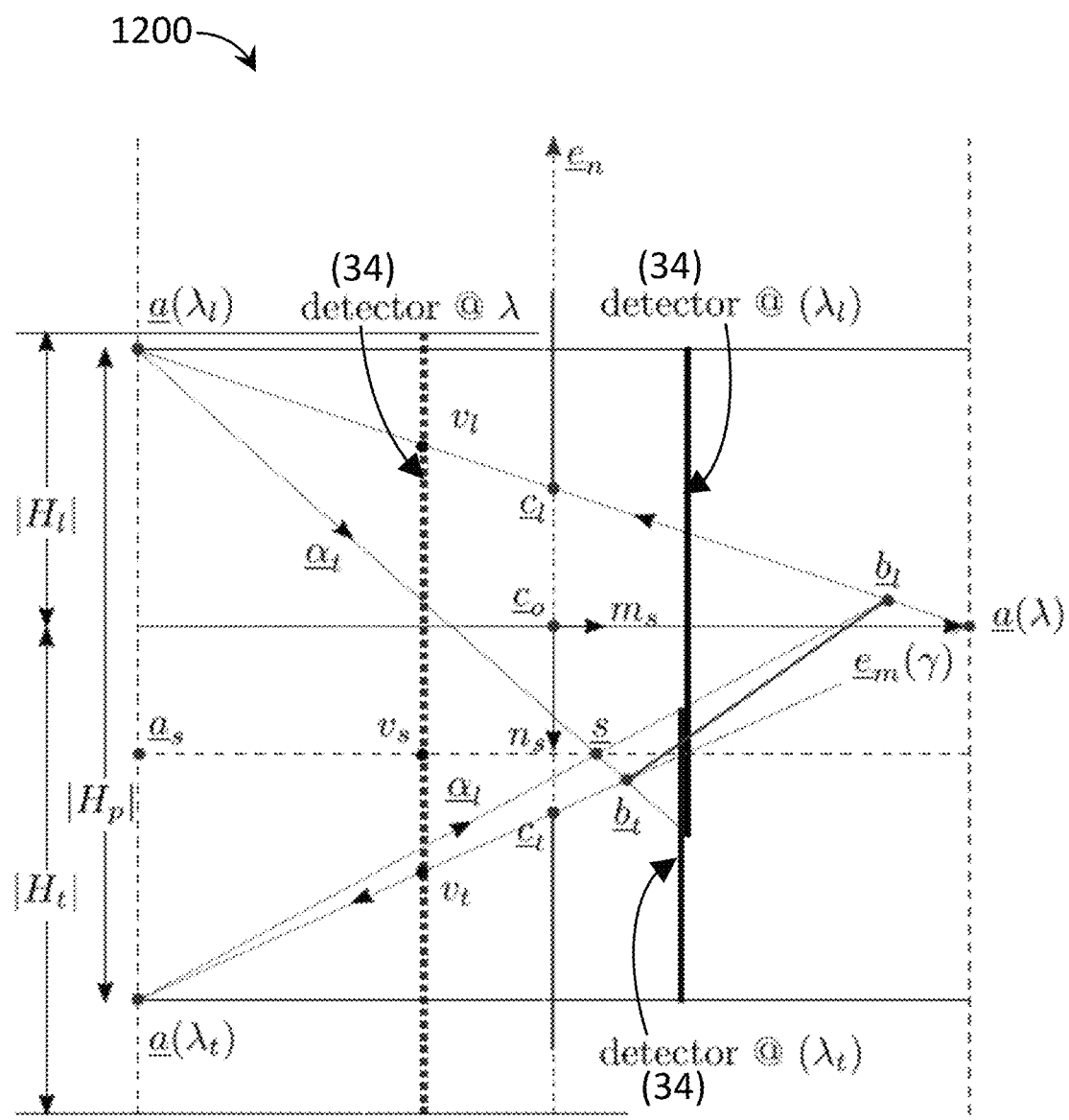
FIG. 12 is an illustration of an exemplary geometry of a large pitch helical data acquisition in the (m, n) coordinate system.

For example, FIGS. 11 and 12 illustrate two exemplary cases of pitch. FIG. 11 illustrates an exemplary geometry 1100 of a small pitch helical data acquisition in an (m, n) coordinate system. FIG. 12 illustrates an exemplary geometry 1200 of a large pitch helical data acquisition in the (m, n) coordinate system.

In the case of small pitch geometry 1100 (FIG. 11), there is always at least one conjugate ray that intersects with the ray to be assessed at the n-axis. In this case, the missing rays can be directly assessed using these conjugate rays.

In the case of large pitch geometry 1200 (FIG. 12), there are situations where no conjugate rays would intersect the ray to be assessed at the n-axis. The following procedure will make sure that the completing reference becomes the n-axis for small pitches according to equation 19:

$$b_l = c_l \text{ if } b_l \cdot e_m < 0$$

$$b_t = c_t \text{ if } b_t \cdot e_m < 0 \quad (19)$$

Next, at step 1020, the method 1000 identifies, for each missing ray $\mathcal{L}(\lambda, u, v)$, its intersection with the completing reference. The intersection is denoted as $b_v$. There are two cases for $b_v$ according to the definition of the completing reference. The value of $b_v$ is defined by equation 20:

$$b_v = \zeta(a(\lambda), d(u,v), b_l, b_t) \text{ if } (v-v_l)(v-v_t) \leq 0$$

$$b_v = \zeta(a(\lambda), d(u,v), c_l, c_t) \text{ if } (v-v_l)(v-v_t) > \quad (20)$$

For small pitches, the above two formulas in equation 20 become identical.

Figure 13:
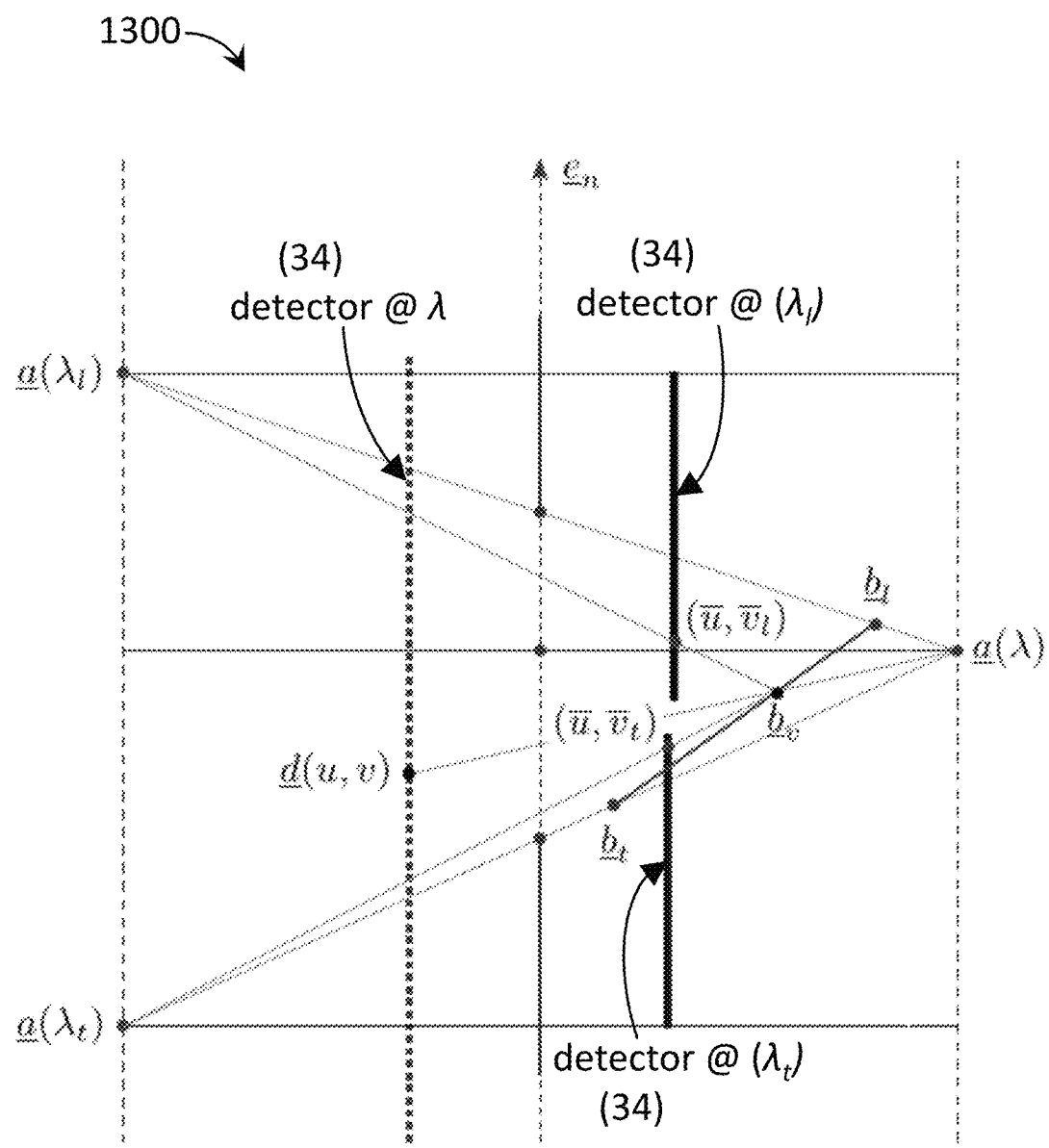
FIG. 13 is an illustration of an exemplary geometry of a large pitch helical data acquisition in an (m, n) coordinate system where the conjugate ray is located inside the Tam-Danielsson window of the current view.
Figure 14:
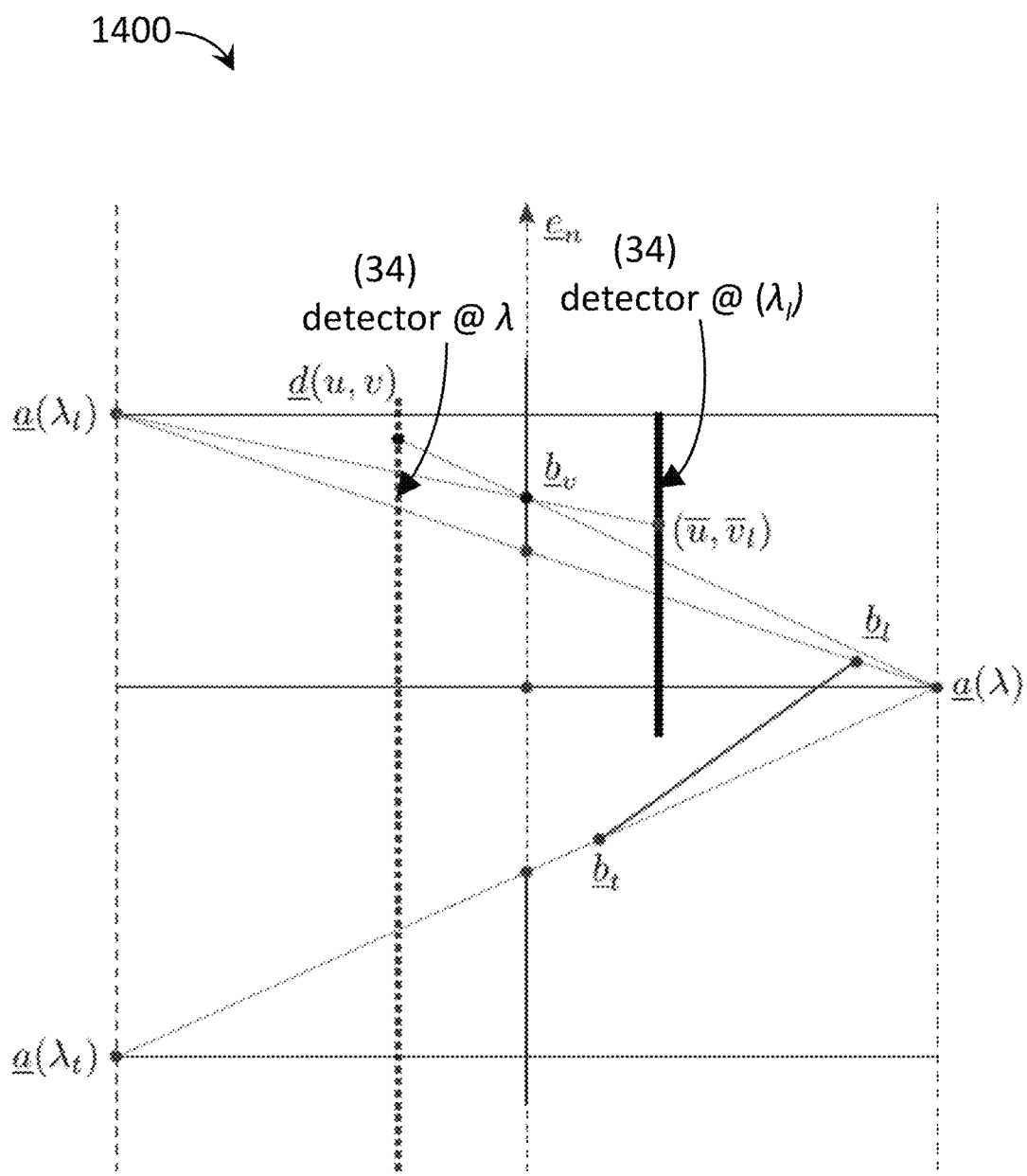
FIG. 14 is an illustration of an exemplary geometry of a large pitch helical data acquisition in the (m, n) coordinate system where the conjugate ray is located outside the Tam-Danielsson window.

For example, FIGS. 13 and 14 illustrate two exemplary cases of large pitch. FIG. 13 illustrates an exemplary geometry 1300 of a large pitch helical data acquisition in an (m, n) coordinate system where the conjugate ray is located inside the Tam-Danielsson window of the current view. FIG. 14 illustrates an exemplary geometry 1400 of a large pitch helical data acquisition in the (m, n) coordinate system where the conjugate ray is located outside the Tam-Danielsson window.

Next, at step 1030, the method 1000 calculates the row indices of the conjugate rays: $\bar{v}_l$ for $a(\lambda_l)$ and $\bar{v}_t$ for $a(\lambda_t)$ (e.g., see FIGS. 12-13). In particular, $\bar{v}_l$ can be calculated using equation 21:

$$\bar{v}_l = -cdir \frac{D_\gamma(\underline{b}_v - \underline{a}(\lambda_l)) \cdot \underline{e}_n}{(\underline{b}_v - \underline{a}(\lambda_l)) \cdot \underline{e}_m}; \quad (21)$$

and $\bar{v}_t$ can be calculated using equation 22:

$$\bar{v}_t = -cdir \frac{D_\gamma(\underline{b}_v - \underline{a}(\lambda_t)) \cdot \underline{e}_n}{(\underline{b}_v - \underline{a}(\lambda_t)) \cdot \underline{e}_m} \quad (22)$$

Next, at step 1040, the method 1000 normalizes the measured value of the conjugate rays according to their cone angles. Let the normalized value corresponding to $a(\lambda_t)$ be $\hat{g}(\lambda_t, \bar{u}, \bar{v}_t)$, and let the normalized value corresponding to $a(\lambda_l)$ be $\hat{g}(\lambda_t, \bar{u}, \bar{v}_l)$. These normalized quantities can be obtained using equation 23:

$$\hat{g}(\lambda_t, \bar{u}, \bar{v}_t) = \frac{\sqrt{v^2 + D_\gamma^2}}{\sqrt{\bar{v}_t^2 + D_\gamma^2}} g(\lambda_t, \bar{u}, \bar{v}_t) \quad (23)$$

$$\hat{g}(\lambda_t, \bar{u}, \bar{v}_l) = \frac{\sqrt{v^2 + D_\gamma^2}}{\sqrt{\bar{v}_l^2 + D_\gamma^2}} g(\lambda_t, \bar{u}, \bar{v}_l)$$

Next, at step 1050, the method 1000 merges the normalized values of the two conjugate rays in the $e_v$ direction. In particular, let $\bar{g}_0(\lambda, u, v)$ be the value after merging, which can be determined by equation 24:

$$\bar{g}_0 = (\lambda, u, v) = w_t(\lambda, u, v)\hat{g}(\lambda_t, \bar{u}, \bar{v}_t) + (1 - w_t(\lambda, u, v))\hat{g}(\lambda_t, \bar{u}, \bar{v}_l), \quad (24)$$

where $$w_t(\lambda, u, v) = \begin{cases} 0 & \text{if } (-cdir \cdot v) \geq (-cdir \cdot v_l) \\ \frac{1}{2}\cos^2\left(\frac{v - v_s}{v_l - v_s} \cdot \frac{\pi}{2}\right) & \text{if } (v - v_s)(v - v_l) < 0 \\ \frac{1}{2}\cos^2\left(\frac{v - v_t}{v_s - v_t} \cdot \frac{\pi}{2}\right) + \frac{1}{2} & \text{if } (v - v_s)(v - v_t) \leq 0 \\ 1 & \text{if } (-cdir \cdot v) < (-cdir \cdot v_t) \end{cases} \quad (25)$$

with $v_s = v_l * |H_t|/(|H_t| + |H_l|) + v_t * |H_l|/(|H_t| + |H_l|)$.

After merging the normalized values of the two conjugate rays in step 1050, exemplary method 1000 for determining the values of the missing rays using measurements of conjugate rays is complete. As introduced above, method 1000 is an exemplary method of determining the values of the missing rays according to step 814 of method 810. Method 810 is an exemplary view completion technique, for example, according to step 710 of the exemplary reconstruction framework 700.

Referring back to FIG. 8, after completion of step 814, method 810 can continue with step 816 to merge the values for the missing rays with the measured data from the current view so that the transition is smooth in the channel direction. Various exemplary methods may be used for step 816.

For example, in one embodiment, the estimated value of the missing ray go defined in equation 24 is directly stitched with the measured data at step 816. This method works perfectly if the object is axial-invariant. However, in the case of an axial-variant object, which is usually the case, this method will result in discontinuity between this estimated data and the measured data, which will cause artifacts in the reconstructed images.

In another embodiment, which may overcome the drawback of direct stitching, a feathering process may be introduced to merge the determined data and the measured data at step 816. Let $[u_L, u_T]$ be the channel range for the feathering process, such that the contribution of the measured data at is 0 at $u_L$ and 1 at $u_T$. To avoid contamination in the region of the measured data, $u_T$ is chosen to be the coordinate of the innermost channel (the one that is closer to $O_d$). Recall that $\hat{g}(\lambda, u, v)$ is the projection data feeding into the reconstruction engine. This value can be calculated using equation 26:

$$\hat{g}(\lambda, u, v) = (1 - w_F(u, u_L, u_T))\bar{g}_0(\lambda u, v)) + w_F(u, u_L, u_T)g(\lambda, u, v), \quad (26)$$

where $w_F$ (U, $u_L$, $u_T$) is a feathering/smoothing function changing from 0 to 1 for channel coordinates from $u_L$ to $u_T$. Also, the first derivative of $w_F$ (U, $u_L$, $u_T$) is 0 at both $u_L$ and $u_T$. There are various functions that can satisfy the above two requirements. In one embodiment, using equation 27:

$$w_F(u, u_L, u_T) = \begin{cases} 0 & \text{if } u < u_L \\ \frac{(u - u_L)^2}{(u - u_L)^2 + (u - u_T)^2} & \text{if } u \in [u_L, u_T] \\ 1 & \text{if } u > u_T \end{cases} \quad (27)$$

While this method provides a smoothing transition between the determined and the measured data along the channel direction, it introduces artifacts due to the reuse of the edge value in the feathering process. These artifacts are especially visible in the projection domain for objects that are axial-invariant.

Figure 15:
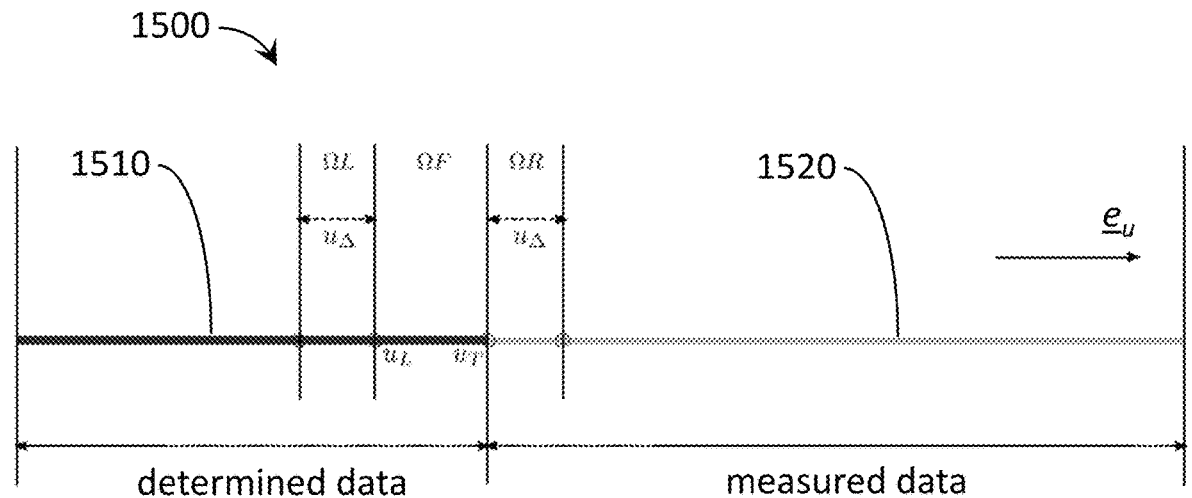
FIG. 15 is an illustration of exemplary merged determined and measured data along the channel direction.

In another embodiment, which can overcome the disadvantages of both of the above methods, another technique implements a fitting and a feathering process at step 816. First the method performs a fitting procedure between the determined and measured data that are adjacent to the feathering zone. Then the fitted data and the determined data are merged using a feathering process. For example, FIG. 15 depicts exemplary merged determined and measured data 1500 along the channel direction. The darker line 1510 on the left refers to the determined data and the lighter line 1520 on the right refers to the measured data. Data belonging to the ranges ΩL and ΩR are used for the fitting process, whereas data belonging to the range ΩF are obtained using a feathering process between the fitted data and the determined data.

Note that during implementation, the above merging process is shift-invariant, and corresponds to fixed u coordinates. Therefore, the feathering function can be pre-calculated and implemented using u indices. Let $\bar{N}$ be the number of channels to be completed and let ΔN be the channels used for feathering. In one embodiment, one way to adaptively select ΔN is according to equation 28:

$$\Delta N = \min(\max(N_0, c_0\bar{N}), c_1\bar{N}), \quad (28)$$

where $0 < c_0 < c_1 < 1$ and $N_0$ is a predefined integer. For example, in one embodiment, $N_0 = 60$, $c_0 = 0.1$ and $c_1 = 0.5$.

After step 816 to merge the determined values for the missing rays with the measured data from the current view so that the transition is smooth in the channel direction, exemplary view completion method 810 is complete. As introduced above, method 810 is an exemplary view completion technique, for example, according to step 710 of the exemplary reconstruction framework 700.

In various embodiments, an x-ray detector 34 offset relative to the virtual centerline 402, such that a completed view of a target requires combining a current view with at least one conjugate view, e.g., due to the offset, during a helical scan, can combine projection data measured from the current view with projection data determined from projection data measured from at least one conjugate view (based on an assessment of missing rays) to reconstruct a target image. The detector 34 can be offset in the channel and/or axial (row) direction. The conjugate views can include a trailing view and/or a leading view during a neighboring rotation. In one embodiment, the x-ray imaging apparatus 10 includes a data processing system configured to receive measured projection data from the current view and the at least one conjugate view, determine values of rays missing in the projection data from the current view based on the measured projection data from the at least one conjugate view, and merge the values of the missing rays with the measured projection data from the current view.

Referring back to FIG. 7, after completion of step 710 to determine ĝ, method 700 can continue with step 720. At step 720, the framework 700 applies differentiating and cone beam (CB) weighting to the projection data feed $\hat{g}(\lambda, u, v)$ to generate $g'_{CB}(\lambda, U, V)$, according to equation 10, as described above. The differentiation operation in step 720 can be important for the reconstruction framework 700 and implemented using a variety of methods.

At step 730, the framework 700 applies a Hilbert transform to $g'_{CB}(\lambda, u, v)$ to generate $g_H(\lambda, U, V)$, according to equation 9, as described above. Next, at step 740, the framework 700 applies a back-projection with 2D aperture weighting to $g_H(\lambda, U, V)$ to generate reconstruction images (f̂(x)), according to equation 7, as described above. Unlike typical 1D aperture weighting, this embodiment uses 2D aperture weighting as defined in equation 11 above. In this embodiment, the 2D aperture weighting can be defined by two separable 1D functions. One function is along the channel direction (denoted by $w_u(u)$), and the other function is along the row direction (denoted by $w_v(v)$). The function $w_u$ is a feathering function and can be defined by $w_F$ (equation 27). In particular, let $u_H$ be the upper bound of the feathering function with a condition that $u_H \in (u_T, umax)$ with umax being the maximum channel coordinate of the detector. Then according to equation 29:

$$w_u(u, u_T, u_H) = w_F(u, u_T, u_H). \quad (29)$$

The function $w_v$ is defined such that the central rows get a weighting 1 and the peripheral ones get a feathering down weighting when the rows are approaching the edges. This 1D row aperture weighting can also be defined using the feathering function, as shown in equation 30:

$$w_v(v, vEmin, vQmin, vQmax, vEmax) = \quad (30)$$
$$\begin{cases} w_F(v, vEmin, vQmin) & \text{if } v < 0 \\ 1 - w_F(v, vQmax, vEmax) & \text{if } v \geq 0 \end{cases},$$

where vEmin and vEmax are the minimum and maximum v coordinates of the detector 34 and vQmin and vQmax specifies where the feathering down starts. In various embodiments, a typical ratio of vQmax/vEmax (or vQmin/vEmin) can be about 0.6, 0.8, etc.

Note that the aperture weighting of step 740 is different from the channel merging process, as it is pixel dependent. After the reconstruction images (f̂(x)) are generated in step 740, exemplary framework 700 is complete.

In various embodiments, processing the projection data includes receiving measured projection data from a current view and at least one conjugate view from an offset detector 34 during a helical imaging scan, determining values of rays missing in the projection data from the current view based on the measured projection data from the at least one conjugate view, and merging the determined values of the missing rays with the measured projection data from the current view to form a completed view of a target. In some embodiments, processing the projection data also includes calculating parameters defining the at least one conjugate view such that the measured projection data from the at least one conjugate view is sufficient to determine the values of rays missing in the projection data from the current view.

In other embodiments, processing the projection data includes differentiating and weighting the merged values forming the completed view of the target, applying a Hilbert transform to the differentiated and weighted data, and back-projecting the transformed data to create a reconstructed image. In some embodiments, back-projecting the transformed data to create the reconstructed image comprises a two-dimensional aperture weighting scheme for data redundancy.

In some embodiments, determining the values of rays missing in the projection data from the current view based on the measured projection data from the at least one conjugate view includes identifying a completing reference, identifying a missing ray intersection with the completing reference, calculating a row index of a conjugate ray associated with the at least one conjugate view, normalizing a measured value of the conjugate ray, and merging normalized values of conjugate rays.

In some embodiments, merging the determined values of the missing rays with the measured projection data from the current view to form the completed view of the target includes fitting the determined values of the missing rays with the measured projection data adjacent to a feathering zone to form fitted data and merging the fitted data with the determined values of the missing rays using a feathering process.

Furthermore, the above x-ray imaging apparatus 10 and data processing techniques include the following features: embodiments use a flat panel detector 34 instead of a curved CT detector; aggressive detector offsets (e.g., 50 cm field-of-view) are allowable to obtain a large FOV, whereas typical mild offsets may be limited, for example, to enlarge a CT FOV (e.g., 10 cm offset (from 50 cm to 70 cm FOV)); data completion and processing methods that are exact if the attenuation coefficient of the scanned object does not vary in the axial direction, which does not hold for typical techniques; and reconstruction methods that are different from the typically known FDK framework.

Figure 16:
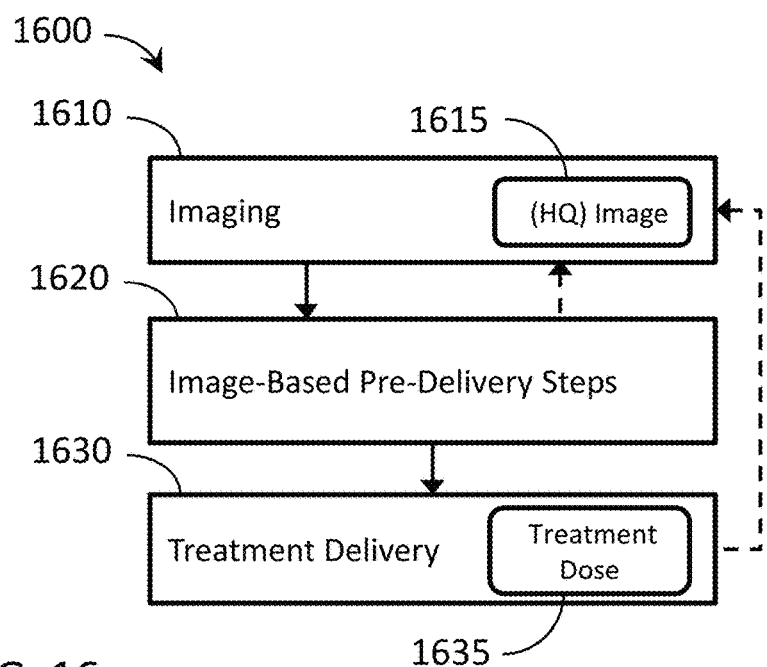
FIG. 16 is a flow chart depicting an exemplary method of IGRT using a radiotherapy device.

FIG. 16 is a flow chart depicting an exemplary method 1600 of IGRT using a radiotherapy device (including, e.g., x-ray imaging apparatus 10). In some embodiments, prior image data of the patient may also be available for use (e.g., a prior image, which may be a previously-acquired planning image, including a prior CT image). Prior data can also include treatment plans, phantom information, models, a priori information, etc. In some embodiments, prior image data is generated by the same imaging/radiotherapy device, but at an earlier time. At step 1610, imaging of a patient is performed using a source of low-energy radiation (e.g., kV radiation from x-ray source 30). In one embodiment, imaging comprises a helical scan with a fan or cone beam geometry. Step 1610 can produce high-quality (HQ) image (s) or imaging data 1615 using the projection data processing techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time.

Next, at step 1620, one or more image-based pre-delivery steps, discussed below, are performed based at least in part on the imaging data 1615 from step 1610. As discussed in more detail below, step 1620 can include determining various parameters associated with the therapeutic treatment and (subsequent) imaging planning. In some embodiments, image-based pre-delivery steps (1620) may require more imaging (1610) before treatment delivery (1630). Step 1620 can include adapting a treatment plan based on the high-quality imaging data 1615 as part of an adaptive radiotherapy routine. In some embodiments, image-based pre-delivery steps 1620 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1630, therapeutic treatment delivery is performed using a source of high-energy radiation (e.g., MV radiation from therapeutic radiation source 20). Step 1630 delivers a treatment dose 1635 to the patient according to the treatment plan. In some embodiments, the IGRT method 1600 may include returning to step 1610 for additional imaging at various intervals, followed by image-based pre-delivery steps (1620) and/or treatment delivery (1630) as required. In this manner the high-quality imaging data 1615 may be produced and utilized during IGRT using one apparatus 10 that is capable of adaptive therapy. As mentioned above, steps 1610, 1620, and/or 1630 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 17:
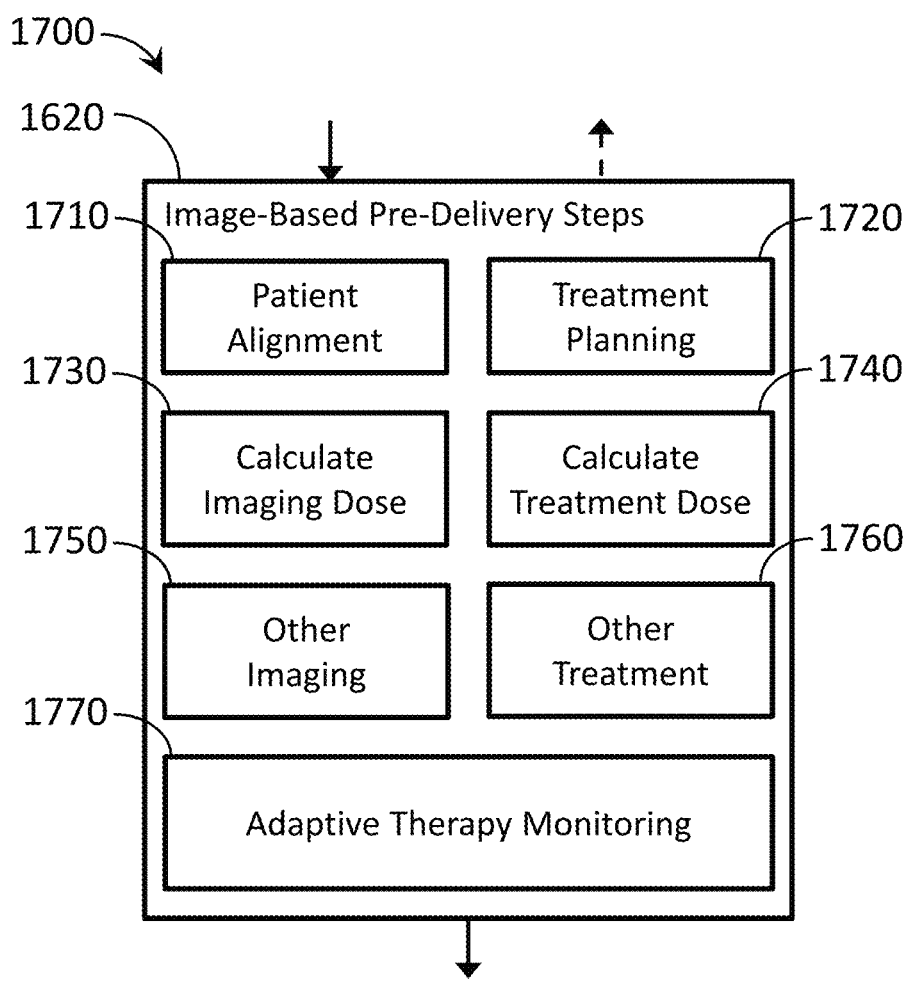
FIG. 17 is a block diagram depicting exemplary image-based pre-delivery steps.

FIG. 17 is a block diagram 1700 depicting exemplary image-based pre-delivery steps/options that may be associated with step 1620 above. It will be appreciated that the above-described x-ray imaging apparatus 10 (e.g., as part of a radiotherapy device) can generate kV images that can be used in a variety of ways, including for image-based pre-delivery steps (1620), without departing from the scope of the present invention. For example, images 1615 generated by the radiotherapy device can be used to align a patient prior to treatment (1710). Patient alignment can include correlating or registering the current imaging data 1615 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the x-ray imaging apparatus 10 can also be used for treatment planning or re-planning (1720). In various embodiments, step 1720 can include confirming the treatment plan, modifying the treatment plan, generating a new treatment plan, and/or choosing a treatment plan from a set of treatment plans (sometimes referred to as "plan of the day"). For example, if the imaging data 1615 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1615 (generated by the x-ray imaging apparatus 10 at step 1610), the imaging data 1615 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the x-ray imaging apparatus 10 can be used to calculate imaging dose (1730), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the x-ray imaging apparatus 10 can be used to calculate treatment dose (1740), which may be used for ongoing determinations of total dose to the patient and/or may be included as part of treatment planning or re-planning.

In accordance with other exemplary use cases, images generated by the x-ray imaging apparatus 10 can be used in connection with planning or adjusting other imaging (1750) and/or other treatment (1760) parameters or plans, including, for example, as part of adaptive therapy and/or treatment plan generation. In accordance with another exemplary use case, images generated by the x-ray imaging apparatus 10 can be used in connection with adaptive therapy monitoring (1770), which can include monitoring treatment delivery and adapting as required.

It should be appreciated that the image-based pre-delivery steps (1620) are not mutually exclusive. For example, in various embodiments, calculate treatment dose (1740) can be a step by itself and/or can be part of adaptive therapy monitoring (1770) and/or treatment planning (1720). In various embodiments, the image-based pre-delivery steps (1620) can be performed automatically and/or manually with human involvement.

The devices and methods described above, including the offset detector and data processing techniques, provide improved kV-generated images of higher quality than conventional in-treatment imaging systems.

Figure 18:
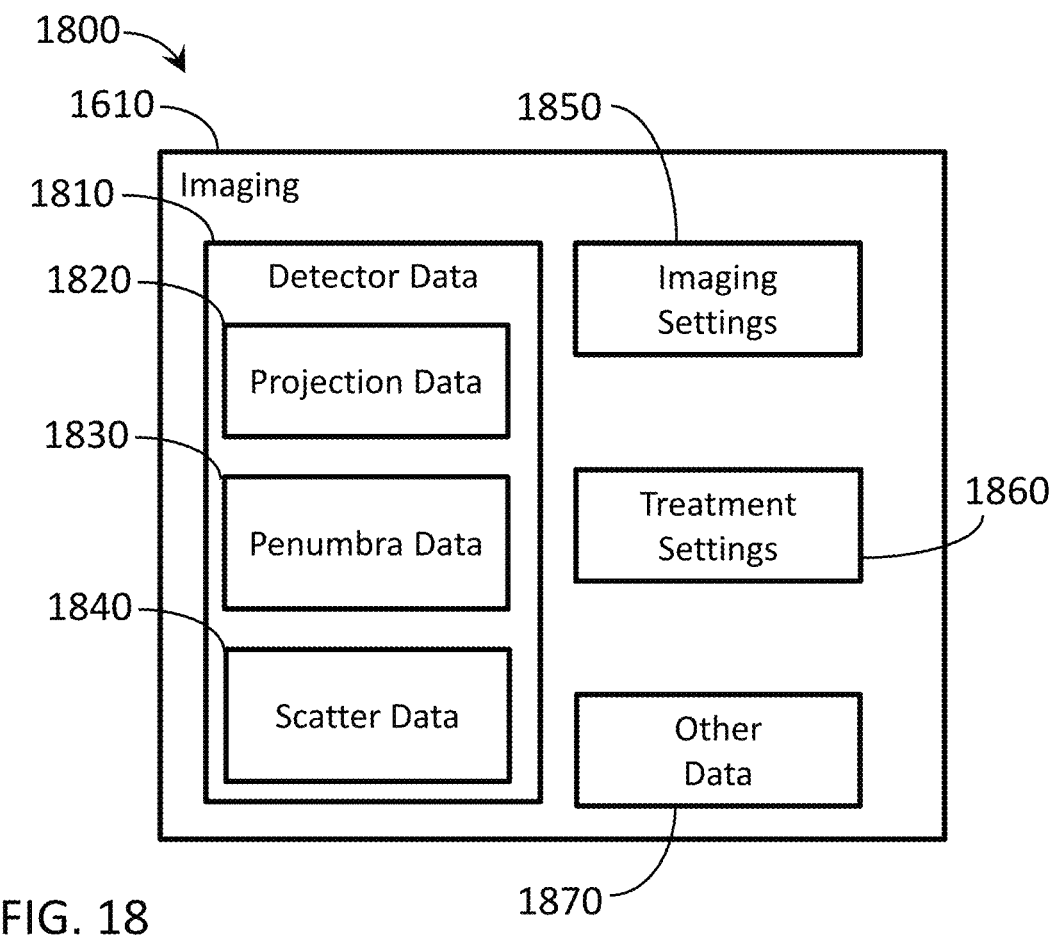
FIG. 18 is a block diagram depicting exemplary data sources that may be utilized during imaging or image-based pre-delivery steps.

FIG. 18 is a block diagram 1800 depicting exemplary data sources that may be utilized during imaging (1610) and/or subsequent image-based pre-delivery steps (1620). Detector data 1810 represents all of the data received by the image radiation detector 34. The projection data 1820 is the data generated by the radiation incident in the collimated beam area. The penumbra data 1830 is the data generated by the radiation incident in the penumbra area. The scatter data 1840 is the data generated by the radiation incident in the peripheral area outside of the penumbra area, which may be referred to as the shadow region(s).

In one embodiment, the penumbra data 1830 may be used to separate or identify the projection and/or scatter data. In some embodiments, the scatter data 1840 can be used to estimate the scatter radiation in the projection data 1820. In another embodiment, the scatter data 1840 can be used to determine the residual effect of the scatter from the therapeutic radiation source 20 (e.g., MV) when the two sources 20, 30 are operated simultaneously or in an interleaved manner.

In this manner, the penumbra data 1830 and/or the scatter data 1840 may be utilized to improve the quality of the images generated by the imaging step 1610. In some embodiments, the penumbra data 1830 and/or the scatter data 1840 may be combined with the projection data 1820 and/or analyzed in view of the applicable imaging settings 1850, treatment settings 1860 (e.g., if simultaneous imaging and treatment radiation), and any other data 1870 associated with the x-ray imaging apparatus 10 at the time of the data collection at the imaging detector 34. In other embodiments, the data may be used for the treatment planning step 1620.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An x-ray imaging apparatus utilizing an offset detector, comprising:
   a rotating x-ray source for emitting a radiation beam within a gantry system, wherein the rotating x-ray source combines with movement of a patient support to create a helical imaging trajectory during a scan;
   an x-ray detector positioned to receive radiation from the x-ray source, wherein the detector is offset relative to a virtual centerline from the x-ray source through an iso-center of the gantry system, such that a completed view of a target requires combining a current view with at least one conjugate view due to the offset, wherein the conjugate view comprises a trailing view or a leading view during a neighboring rotation;
   a beamformer configured to adjust a shape of the radiation beam emitted by the x-ray source towards the offset detector; and
   a data processing system configured to combine projection data measured from the current view with projection data determined from projection data measured from the at least one conjugate view to reconstruct a target image.

2. The apparatus of claim 1, wherein the detector is offset relative to the virtual centerline in a channel direction.

3. The apparatus of claim 1, wherein the detector is offset relative to the virtual centerline in an axial direction.

4. The apparatus of claim 1, wherein the detector is offset relative to the virtual centerline in a channel direction and in an axial direction.

5. The apparatus of claim 1, wherein the at least one conjugate view comprises a plurality of conjugate views.

6. The apparatus of claim 1, wherein the at least one conjugate view comprises the trailing view and the leading view during neighboring rotations.

7. The apparatus of claim 1, wherein the beamformer is configured to adjust the shape of the radiation beam by at least one of rotation or translation of x-ray attenuated material of the beamformer.

8. The apparatus of claim 1, wherein the beamformer is configured to adjust the shape of the radiation beam into a rectangle or parallelogram.

9. The apparatus of claim 1, wherein the data processing system is further configured to:
   receive measured projection data from the current view and the at least one conjugate view;
   determine values of rays missing in the projection data from the current view based on the measured projection data from the at least one conjugate view; and
   merge the values of the missing rays with the measured projection data from the current view.

10. A method of processing projection data from an x-ray imaging apparatus utilizing an offset detector, comprising:
    receiving at a data processing system measured projection data from a current view and at least one conjugate view from the offset detector during a helical imaging scan;
    determining, using the data processing system, values of rays missing in the projection data from the current view based on the measured projection data from the at least one conjugate view; and
    merging, using the data processing system, the determined values of the missing rays with the measured projection data from the current view to form a completed view of a target.

11. The method of claim 10, further comprising:
    calculating parameters defining the at least one conjugate view such that the measured projection data from the at least one conjugate view is sufficient to determine the values of rays missing in the projection data from the current view.

12. The method of claim 10, further comprising:
    differentiating and weighting the merged values forming the completed view of the target;
    applying a Hilbert transform to the differentiated and weighted data; and
    back-projecting the transformed data to create a reconstructed image.

13. The method of claim 12, wherein back-projecting the transformed data to create the reconstructed image comprises a two-dimensional aperture weighting scheme for data redundancy.

14. The method of claim 10, wherein determining the values of rays missing in the projection data from the current view based on the measured projection data from the at least one conjugate view comprises:
identifying a completing reference;
identifying a missing ray intersection with the completing reference;
calculating a row index of a conjugate ray associated with the at least one conjugate view;
normalizing a measured value of the conjugate ray; and
merging normalized values of conjugate rays.

15. The method of claim 10, wherein merging the determined values of the missing rays with the measured projection data from the current view to form the completed view of the target comprises:
fitting the determined values of the missing rays with the measured projection data adjacent to a feathering zone to form fitted data; and
merging the fitted data with the determined values of the missing rays using a feathering process.

16. The method of claim 10, wherein the offset detector is offset relative to a virtual centerline in a channel direction.

17. The method of claim 10, wherein the offset detector is offset relative to a virtual centerline in an axial direction.

18. The method of claim 10, wherein the at least one conjugate view comprises at least one of a trailing view or a leading view during a neighboring rotation.

19. The method of claim 10, wherein the at least one conjugate view comprises a trailing view and a leading view during neighboring rotations.

20. A radiotherapy delivery device comprising:
a rotatable gantry system positioned at least partially around a patient support;
a first source of radiation coupled to the rotatable gantry system, the first source of radiation being configured as a source of therapeutic radiation;
a second source of radiation coupled to the rotatable gantry system, the second source of radiation being configured as a source of imaging radiation having an energy level less than the source of therapeutic radiation, wherein the rotatable gantry system combines with movement of the patient support to create a helical imaging trajectory during a scan;
a radiation detector coupled to the rotatable gantry system and positioned to receive radiation from the second source of radiation, wherein the detector is offset relative to a virtual centerline from the second source of radiation through an iso-center of the gantry system, such that a completed view of a target requires combining a current view with at least one conjugate view;
a beamformer configured to adjust a shape of the radiation beam emitted by the second source of radiation for the offset detector; and
a data processing system configured to:
receive measured projection data from the current view and the at least one conjugate view;
determine values of rays missing in the projection data from the current view based on the measured projection data from the at least one conjugate view;
merge the values of the missing rays with the measured projection data from the current view; and
reconstruct a target image based on the merged data for use during adaptive IGRT.

* * * * *